United States Patent
Hamada et al.

(10) Patent No.: US 8,956,569 B2
(45) Date of Patent: Feb. 17, 2015

(54) SAMPLE TESTING SYSTEM WITH AUTOMATED CONTROL OF SAMPLE RETESTING

(75) Inventors: Yuichi Hamada, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 715 days.

(21) Appl. No.: 12/644,433

(22) Filed: Dec. 22, 2009

(65) Prior Publication Data

US 2010/0159603 A1   Jun. 24, 2010

(30) Foreign Application Priority Data

Dec. 22, 2008  (JP) ................................. 2008-325846
Nov. 27, 2009  (JP) ................................. 2009-270464

(51) Int. Cl.
- *G01N 35/04* (2006.01)
- *G01N 35/02* (2006.01)
- *G01N 35/00* (2006.01)

(52) U.S. Cl.
CPC .............. *G01N 35/00* (2013.01); *G01N 35/026* (2013.01); *G01N 35/04* (2013.01); *G01N 2035/0413* (2013.01)
USPC ................................. 422/65; 436/47; 436/48

(58) Field of Classification Search
CPC ... G01N 35/026; G01N 35/028; G01N 35/04; G01N 2035/0415; G01N 2035/0413
USPC .......................................... 436/47, 48; 422/65
See application file for complete search history.

(56) References Cited

U.S. PATENT DOCUMENTS

| 6,117,392 A | * | 9/2000 | Hanawa et al. | .................. 422/65 |
| 6,314,332 B1 | * | 11/2001 | Kida | .............................. 700/113 |
| 2006/0216199 A1 | | 9/2006 | Koike | |
| 2007/0207056 A1 | | 9/2007 | Veiner et al. | ..................... 422/63 |

FOREIGN PATENT DOCUMENTS

JP         H6-770         1/1994

* cited by examiner

*Primary Examiner* — Yelena G Gakh
*Assistant Examiner* — Michelle Adams
(74) *Attorney, Agent, or Firm* — Brinks Gilson & Lione

(57) ABSTRACT

A sample testing system comprising: a transporting apparatus; a testing apparatus for obtain a sample and performing testing on the obtained sample; and a controller. The controller executes operation of: controlling the transporting apparatus so as to transport the sample rack in first direction, such that each sample container held in a sample rack is transported to a obtaining position on which the testing apparatus obtains a sample and then the sample rack is transported toward the second position; changing, when retesting of a sample contained in a sample container is necessary, the transporting direction from the first direction to second direction, and then controlling the transporting apparatus so as to transport the sample container accommodating the sample, for which retesting is necessary, to the obtaining position again. Sample testing method and a computer program product are also disclosed.

8 Claims, 22 Drawing Sheets

SAMPLE TESTING SYSTEM WITH AUTOMATED CONTROL OF SAMPLE RETESTING

RELATED APPLICATIONS

This application claims priority under 35 U.S.C. §119 to Japanese Patent Application Nos. JP2008-325846 filed on Dec. 22, 2008 and JP2009-270464 filed on Nov. 27, 2009, the entire contents of which are hereby incorporated by reference.

FIELD OF THE INVENTION

The present invention relates to a sample testing system, a sample testing method, and a computer program product. The present invention particularly relates to: a sample testing system that includes a transporting apparatus for transporting sample racks each capable of holding a plurality of samples; a sample testing method for transporting the sample racks each capable of holding a plurality of samples and testing samples held by the sample rack; and a computer program product for controlling the transporting apparatus so as to transport the sample racks each capable of holding a plurality of samples.

BACKGROUND OF THE INVENTION

Conventionally, there are known sample testing systems that include a transporting apparatus for transporting sample racks each capable of holding a plurality of samples (see, e.g., US Application Publication 2006/0216199).

US Application Publication 2006/0216199 discloses a sample testing system that includes: a transverse feeder (a transporting apparatus) for transversely feeding racks each holding a plurality of samples; engagement claws for feeding each rack to a transverse feed start position on the transverse feeder (i.e., to the end of the upstream side of the transverse feeder); and a blood analyzer for testing samples held in each rack that has been transversely fed by the transverse feeder. In this sample testing system, the transverse feeder sequentially and transversely feeds the racks from the transverse feed start position in a forward direction, thereby supplying the samples held in each rack to the analyzer in order of sequence in which the samples are held therein. Each time a sample is supplied to a sample supplying position that is located at a substantially central position on the transverse feeder, the analyzer obtains the sample from its rack to analyze the sample. When obtainment of sample by the analyzer is performed, the transverse feeder further transversely feeds the rack in the forward direction with respect to the sample supplying position so as to dispose the next sample held in the rack at the sample supplying position, thereby supplying the next sample to the analyzer. When the analysis proceeds in this manner, there is a case where the analyzer determines as a result of the analysis that retesting of a sample is necessary. In this case, since the sample needed to be retested, has already been fed transversely in the forward direction from the sample supplying position, it is necessary to transversely feed the rack in the reverse direction such that the sample needed to be retested is disposed at the sample supplying position again. In the sample testing system of US Application Publication 2006/0216199, in such a case, the rack is first transversely fed in the reverse direction to the transverse feed start position (i.e., to the end of the upstream side of the transverse feeder). Then, the rack is transversely fed in the forward direction again, whereby the sample needed to be retested is supplied to the analyzer (i.e., to the sample supplying position).

In the sample testing system described in US Application Publication 2006/0216199, when the rack is transversely fed in the reverse direction for retesting, the sample needed to be retested is once located at the sample supplying position during the transverse feeding. Nevertheless, the rack needs to be transported, passing through the sample supplying position, to the transverse feed start position. Further, the rack also needs to be transversely fed in the forward direction again from the transverse feed start position to the sample supplying position.

SUMMARY OF THE INVENTION

The scope of the invention is defined solely by the appended claims, and is not affected to any degree by the statements within this summary.

A first aspect of the present invention is a sample testing system comprising: a transporting apparatus comprising a transporting member capable of transporting a sample rack between a first position and a second position in a first direction from the first position toward the second position and in a second direction opposite to the first direction, wherein the sample rack holds a plurality of sample containers in a plurality of sample holding positions; a testing apparatus for obtaining a sample from each sample container held in the sample rack that has been transported by the transporting member to a third position located between the first position and the second position, and for performing measurement on the obtained sample; and a controller including a memory under control of a processor, the memory storing instructions enabling the processor to carry out operations comprising: controlling the transporting member so as to transport the sample rack from the first position in the first direction, such that each sample container held in the sample rack is transported to the third position and then the sample rack is transported toward the second position; changing, when retesting of a sample contained in a sample container held in the sample rack is necessary, the transporting direction of the transporting member from the first direction to the second direction, and then controlling the transporting member so as to transport the sample container accommodating the sample, for which retesting is necessary, to the third position again.

A second aspect of the present invention is a sample testing method comprising: transporting a sample rack that holds a plurality of sample containers in a first direction from a first position toward a second position, such that each sample container held in the sample rack is transported to a third position located between the first position and the second position; obtaining a sample from each sample container located on the third position, and performing measurement on the sample; obtaining a measurement result of the sample, and determining based thereon whether or not retesting of the sample is necessary; transporting the sample rack toward the second position; and changing, when retesting of a sample contained in a sample container held in the sample rack is necessary, the transporting direction of the sample rack from the first direction to a second direction that is opposite to the first direction, and then transporting the sample container containing the sample, for which retesting is necessary, to the third position again.

A third aspect of the present invention is a computer program product for a sample testing system comprising: a transporting apparatus comprising a transporting member capable of transporting a sample rack; a testing apparatus for obtaining a sample from a sample container and performing measurement on the sample; and a computer, the computer program product comprising a computer readable medium for storing instructions enabling the computer to carry out operations comprising: controlling the transporting member so as to transport a sample rack in a first direction from a first position toward a second position such that each sample container held in the sample rack is transported to a third position located between the first position and the second position, wherein the sample rack holds a plurality of sample containers in a plurality of sample holding positions; controlling the testing apparatus so as to obtain a sample from each sample container located on the third position, and to perform measurement on the sample; controlling the transporting member so as to transport the sample rack toward the second position; and changing, when retesting of a sample contained in a sample container held in the sample rack is necessary, the transporting direction of the sample rack from the first direction to a second direction that is opposite to the first direction, and then controlling the transporting member so as to transport the sample container containing the sample, for which retesting is necessary, to the third position again.

DETAILED DESCRIPTION OF THE PREFERRED EMBODIMENTS

Hereinafter, an embodiment of a sample testing system of the present invention will be described in detail with reference to the accompanying drawings.

Described below with reference to FIGS. 1 to 9 is an overall configuration of a blood analyzer 1 according to the embodiment of the present invention. Note that the present embodiment describes a case where the present invention is applied in the blood analyzer 1 that is an example of the sample testing system.

Figure 1:
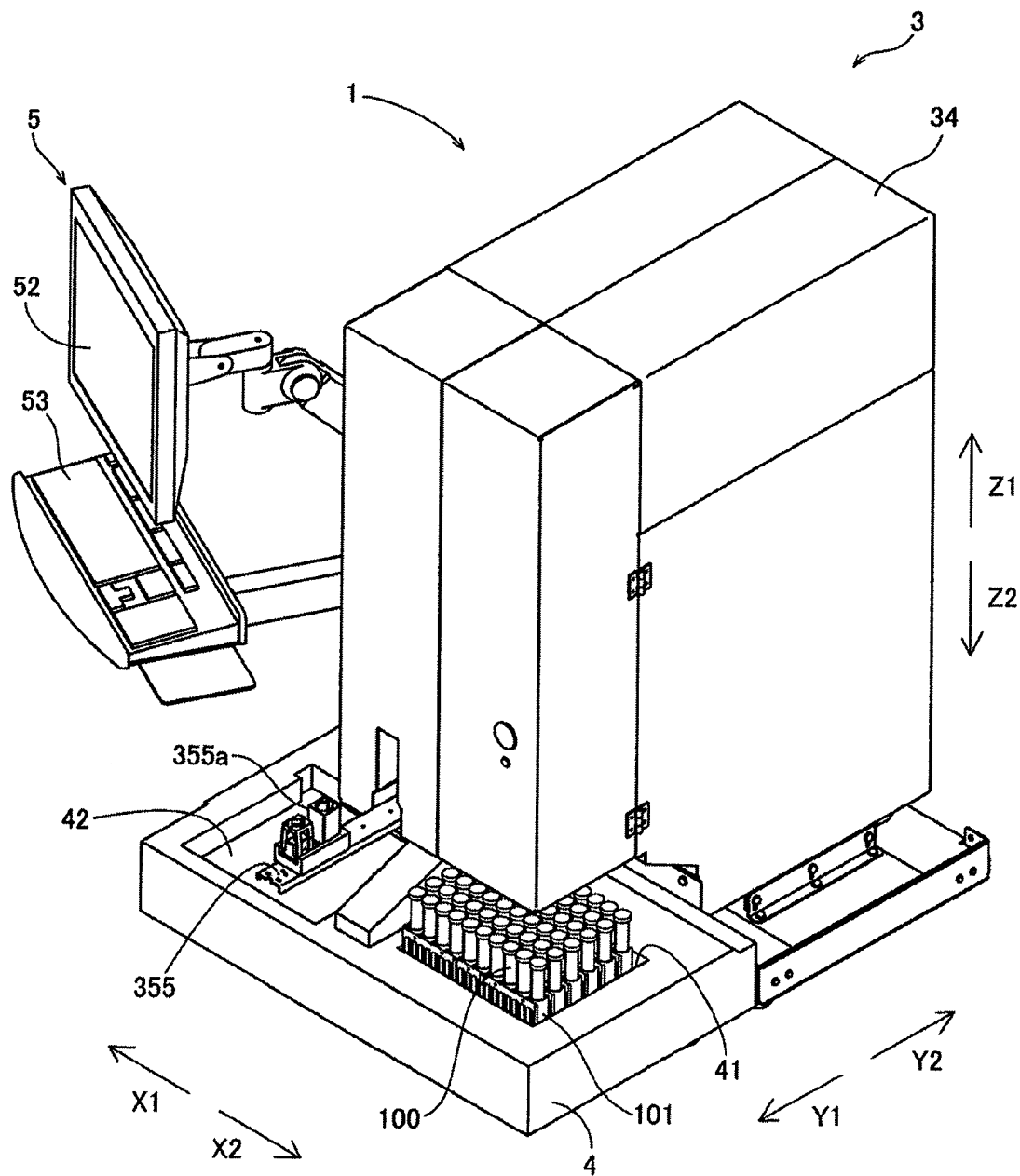
FIG. 1 is a perspective view showing an overall configuration of a blood analyzer according to an embodiment of the present invention.

The blood analyzer 1 according to the present embodiment is connected to a host computer 2 (see FIG. 2), and, as shown in FIG. 1, includes: a measurement unit 3; a sample transporting apparatus (sampler) 4 disposed in front of the measurement unit 3 (i.e., disposed on an arrow Y1 direction side); and a control apparatus 5 structured as a PC (Personal Computer) that is electrically connected to the measurement unit 3 and the sample transporting apparatus 4.

Figure 2:
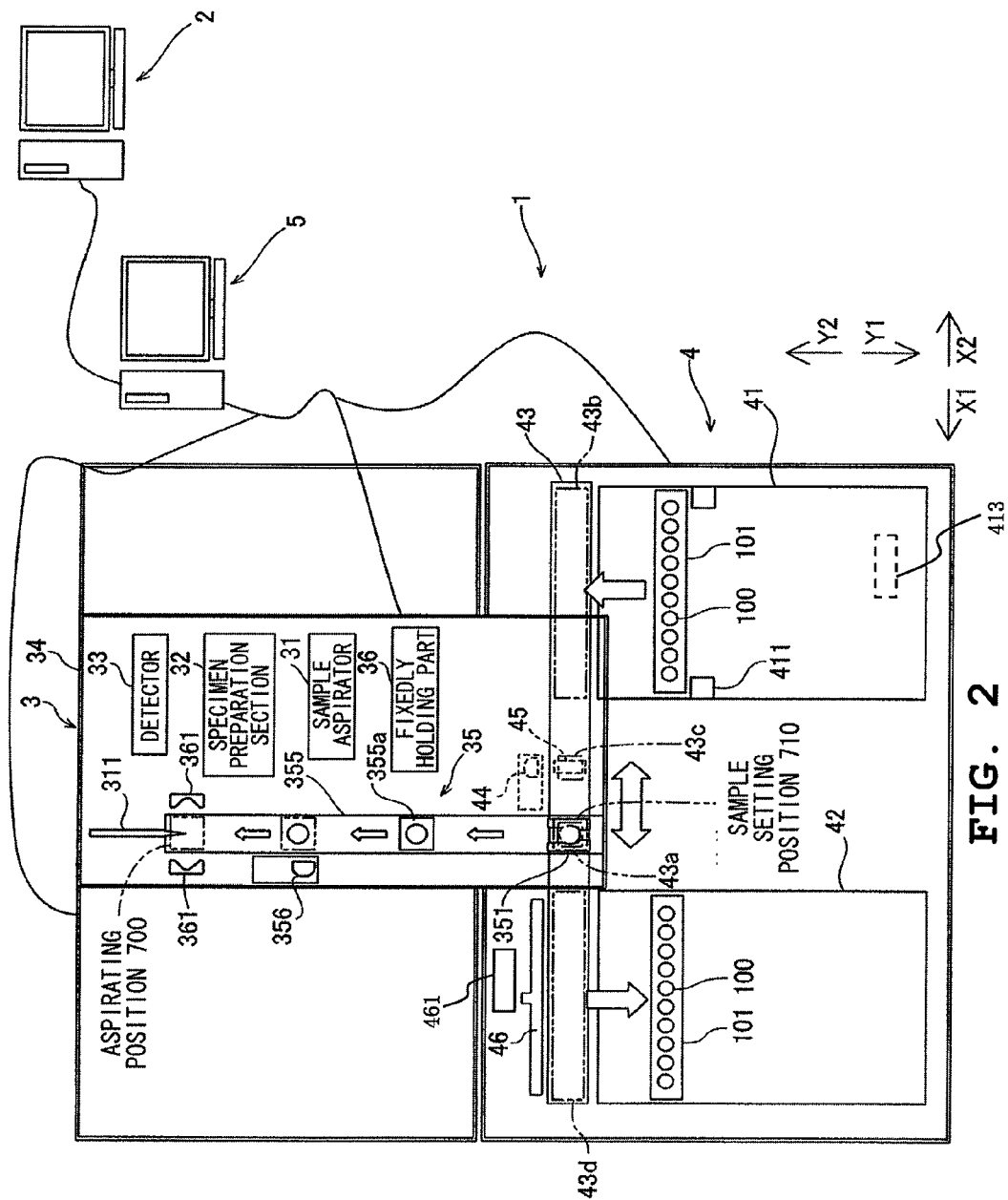
FIG. 2 is a schematic diagram showing a measurement unit and a sample transporting apparatus of the blood analyzer according to the embodiment shown in FIG. 1.

As shown in FIG. 2, the measurement unit 3 includes: a sample aspirator 31 for aspirating a blood sample from a sample container (test tube) 100; a specimen preparation section 32 for preparing a detection specimen from the blood aspirated by the sample aspirator 31; and a detector 33 for detecting blood cells from the detection specimen prepared by the specimen preparation section 32.

The measurement unit 3 further includes: a unit cover 34 for accommodating therein the sample aspirator 31, the specimen preparation section 32, and the like; a sample container transporter 35 for loading a sample container 100 into the inside of the unit cover 34 and for transporting the sample container 100 to an aspirating position 700 of the sample aspirator 31; and a fixedly holding part 36 for fixedly holding the sample container 100 in the aspirating position 700.

As shown in FIG. 2, the sample aspirator 31 includes a piercer 311. The tip of the piercer 311 is formed so as to be able to penetrate (pierce) through a below-described sealing cap 100a (see FIG. 4) of a sample container 100. Further, the piercer 311 is configured to move in vertical directions (arrow Z1 and Z2 directions) through an operation of a piercer drive section that is not shown.

The detector 33 is configured to perform RBC detection (detection of red blood cells) and PLT detection (detection of platelets) by the sheath flow DC detection method, and to perform HGB detection (detection of hemoglobin in blood) by the SLS-hemoglobin method. The detector 33 is also configured to perform WBC detection (detection of while blood cells) by flow cytometry using a semiconductor laser. Detection results obtained by the detector 33 are transmitted to the control apparatus 5 as measurement data (measurement results) of a sample. Note that the measurement data is used as a basis for final analysis results (such as a red blood count, platelet count, amount of hemoglobin, white blood count, and the like) to be provided to a user.

Figure 3:
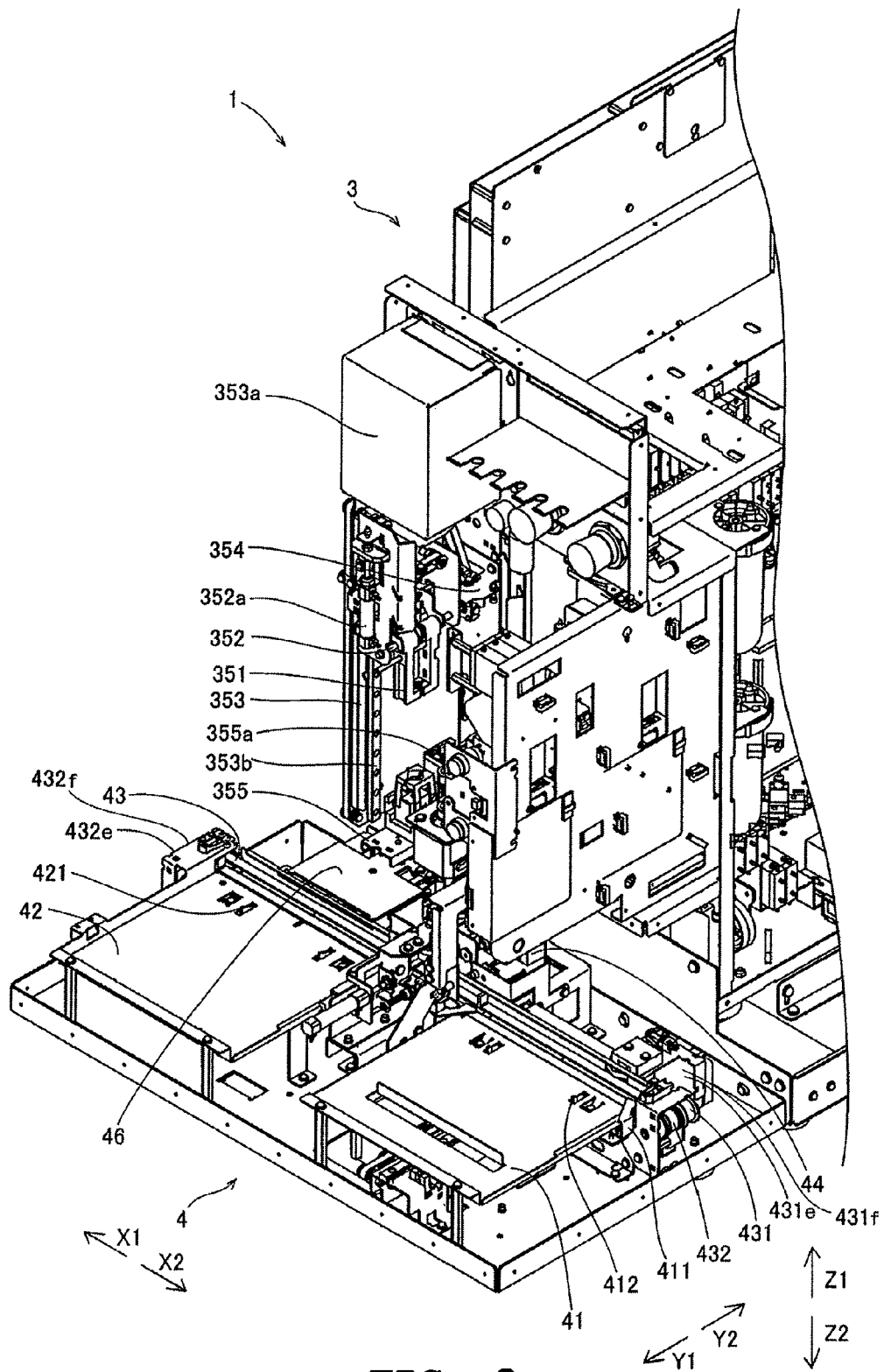
FIG. 3 is a perspective view showing the measurement unit and the sample transporting apparatus of the blood analyzer according to the embodiment shown in FIG. 1.

As shown in FIG. 3, the sample container transporter 35 has: a hand part 351 capable of holding a sample container 100; an opening/closing part 352 for opening/closing the hand part 351; a vertically moving part 353 for rectilinearly moving the hand part 351 in vertical directions (the arrow Z1 and Z2 directions); and an agitator 354 for moving the hand part 351 in the vertical directions (the arrow Z1 and Z2 directions) in a swinging manner. Further, as shown in FIG. 2, the sample container transporter 35 has: a sample container moving part 355 for horizontally moving a sample container 100 in the arrow Y1 and Y2 directions; and a bar code reader 356.

The hand part 351 is disposed above a transporting path on which a rack 101 is transported by the sample transporting apparatus 4. The hand part 351 is configured to, when a sample container 100 has been transported by the sample transporting apparatus 4 to a below-described loading position 43a (see FIG. 2), move downward (in the arrow Z2 direction) and then be caused by the opening/closing part 352 to open and close to hold the sample container 100 that is accommodated in the rack 101.

Further, the hand part 351 is configured to move the held sample container 100 upward (in the arrow Z1 direction) to remove the sample container 100 from the rack 101, and then be moved in a swinging manner by the agitator 354 (e.g., 10 reciprocating swinging movements). In this manner, the hand part 351 is capable of agitating the blood contained in the held sample container 100. The hand part 351 is configured to move, after the agitation has ended, downward (in the arrow Z2 direction) and then be caused by the opening/closing part 352 to release the holding of the sample container 100. To be specific, the hand part 351 is configured to set the sample container 100 into a sample setting part 355a that has been moved by the sample container moving part 355 to a sample setting position 710 (see FIG. 2). Note that, as shown in FIG. 2, the loading position 43a and the sample setting position 710 coincide with each other when viewed in a plan view.

The opening/closing part 352 is configured to cause, based on the dynamics of an air cylinder 352a, the hand part 351 to open and close so as to hold a sample container 100.

The vertically moving part 353 is configured to move, based on the dynamics of a stepping motor 353a, the hand part 351 along a rail 353b in the vertical directions (the arrow Z1 and Z2 directions).

The agitator 354 is configured to move the hand part 351 in the vertical directions (the arrow Z1 and Z2 directions) in a swinging manner based on the dynamics of a stepping motor that is not shown.

As shown in FIG. 1, the sample container moving part 355 has the sample setting part 355a, and is capable of moving the sample setting part 355a to predetermined positions in accordance with operations performed in a measurement process. To be specific, the sample container moving part 355 is capable of disposing the sample setting part 355a in the aspirating position 700 and the sample setting position 710 shown in FIG. 2.

The bar code reader 356 is configured to read a bar code 100b (shown in FIG. 4) affixed to each sample container 100. The bar code 100b of each sample container 100 is uniquely assigned to the sample therein, and used to manage analysis results of each sample.

The fixedly holding part 36 is configured to fixedly hold a sample container 100 having been moved to the aspirating position 700. To be specific, as shown in FIG. 2, the fixedly holding part 36 has a pair of chuck parts 361. The pair of chuck parts 361 are configured to move closer toward each other so as to hold the sample container 100 therebetween.

As shown in FIGS. 2 and 3, the sample transporting apparatus 4 includes: an unanalyzed rack holder 41 capable of holding a plurality of racks 101 each accommodating sample containers 100 that contain unanalyzed samples; an analyzed rack holder 42 capable of holding a plurality of racks 101 each accommodating sample containers 100 that contain samples having been analyzed; a rack transporter 43 for transversely feeding each rack 101 in the arrow X1 and X2 directions; a bar code reader 44; a presence/absence detection sensor 45 (see FIG. 2) for detecting presence/absence of a sample container 100; a rack feed-out part 46 for moving a rack 101 to the inside of the analyzed rack holder 42; and a sample amount detector (not shown) for detecting the amount of sample (blood) contained in a sample container 100 held in a rack 101.

The unanalyzed rack holder 41 has a rack feed-in part 411, and is configured such that the racks 101 held in the unanalyzed rack holder 41 are pushed, one by one, to the rack feed-in position 43b (see FIG. 2) on the rack transporter 43 by the rack feed-in part 411 moving in the arrow Y2 direction. The rack feed-in part 411 is configured to be able to move the racks 101 only toward the rack transporter 43 side (toward the arrow Y2 direction side). That is, the unanalyzed rack holder 41 is not provided with a rack returning mechanism for returning a rack 101 present on the rack transporter 43 to the unanalyzed rack holder 41. Also, the rack feed-in part 411 is configured to be driven by a stepping motor 413 provided below the unanalyzed rack holder 41. Further, the unanalyzed rack holder 41 has a restricting portion 412 (see FIG. 3) near the rack transporter 43, and is configured to restrict, by the restricting portion 412, the movement of the racks 101 such that once a rack 101 is pushed onto the rack transporter 43, the rack 101 does not return to the inside of the unanalyzed rack holder 41.

The analyzed rack holder 42 has a restricting portion 421 (see FIG. 3) near the rack transporter 43, and is configured to restrict, by the restricting portion 421, the movement of the racks 101 such that once a rack 101 is moved to the inside of the analyzed rack holder 42, the rack 101 does not return to the rack transporter 43.

Figure 5:
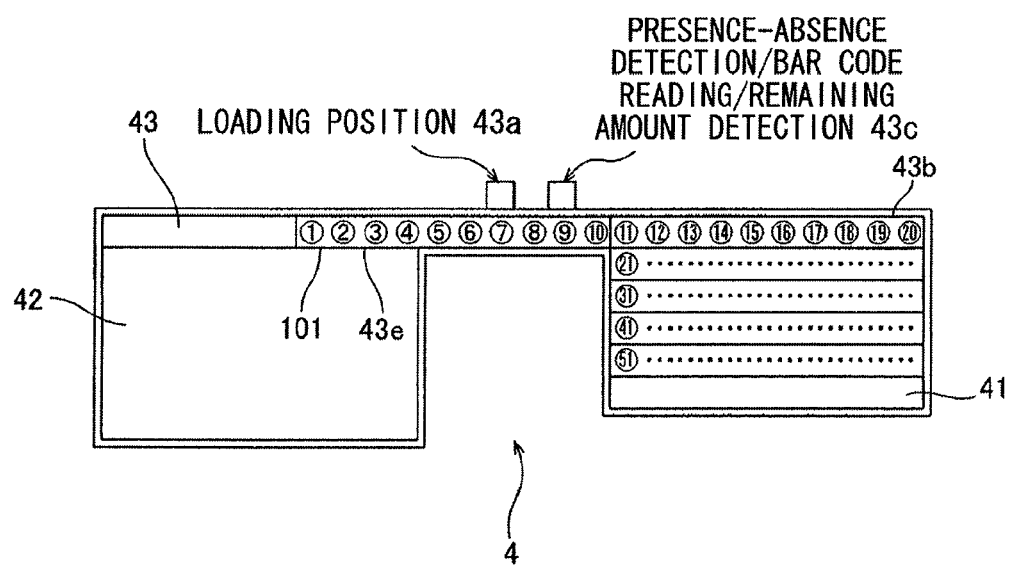
FIG. 5 is a schematic diagram illustrating the sample transporting apparatus of the blood analyzer according to the embodiment shown in FIG. 1.

As shown in FIG. 2, the rack transporter 43 is configured to transversely feed a rack 101 having been fed to the rack feed-in position 43b, in a downstream transporting direction (i.e., the arrow X1 direction) in which to transport the rack 101 to a below-described rack collection position 43d, thereby sequentially disposing the sample containers 100, which are held in the rack 101, to a detection position 43c and to the loading position 43a at which the sample containers 100 are supplied to the measurement unit 3. At the detection position 43c, the presence/absence detection sensor 45 detects presence or absence of a sample container 100, the bar code reader 44 reads the bar code 100b of the sample container 100, and the sample amount detector (not shown) detects the amount of sample (blood) contained in the sample container 100. These operations are sequentially performed on each sample container. The rack transporter 43 is configured to be able to transversely feed the rack 101 to the rack collection position 43d that is located on the rack transporter 43 at a position between the analyzed rack holder 42 and the rack feed-out part 46. FIG. 5 shows a case where a rack 101 is disposed at a feed-in limit position (a position that is nearest to, but does not overlap with, the rack feed-in position 43b) 43e. Here, the end of the rack 101, the end being on the upstream side in the direction of transporting the rack 101 from the rack feed-in position 43b to the rack collection position 43d (i.e., the end of the arrow X2 direction side of the rack 101), is located so as to be adjacent to the end of the rack feed-in position 43b, the end being on the downstream side of the transporting direction (i.e., the end of the arrow X1 direction side of the rack feed-in position 43b). In this case, the location of the loading position 43a coincides with a position of a sample container 100 that is held, in the rack 101, at the seventh sample container portion 101b counted from the downstream side (the arrow X1 direction side) of the transporting direction. In other words, even if a subsequent rack 101 has been fed to the rack feed-in position 43b, it is possible to load the seventh and the following sample containers 100 of a preceding rack 101 into the measurement unit 3.

Figure 6:
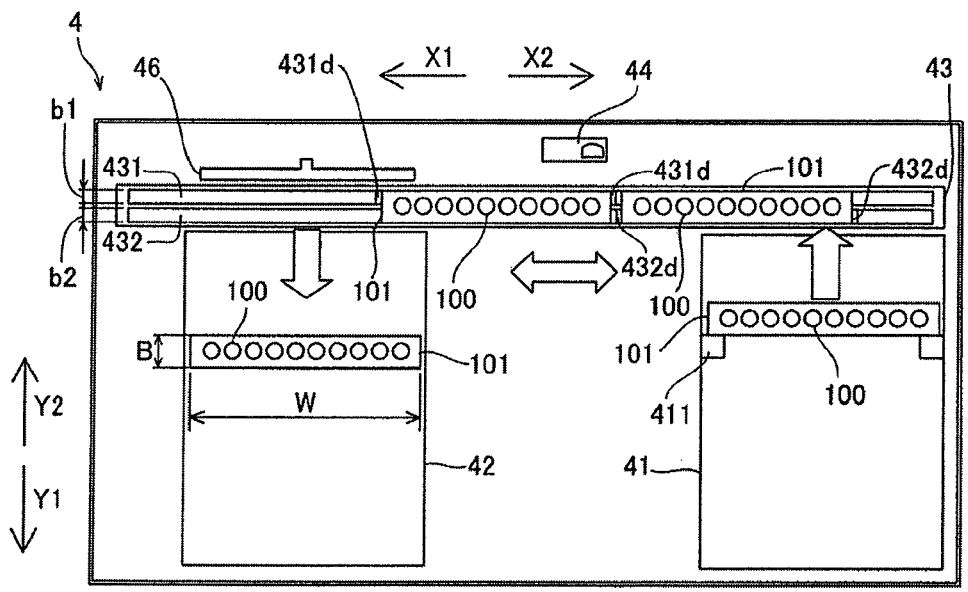
FIG. 6 is a plan view illustrating the sample transporting apparatus of the blood analyzer according to the embodiment shown in FIG. 1.
Figure 7:
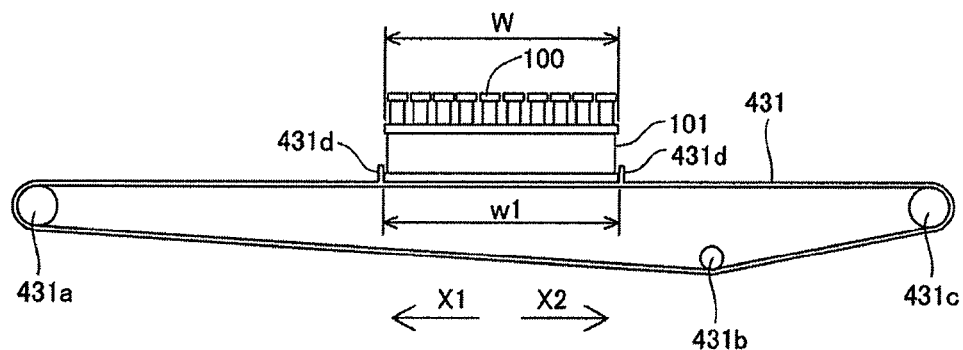
FIG. 7 is a side view illustrating the sample transporting apparatus of the blood analyzer according to the embodiment shown in FIG. 1.
Figure 8:
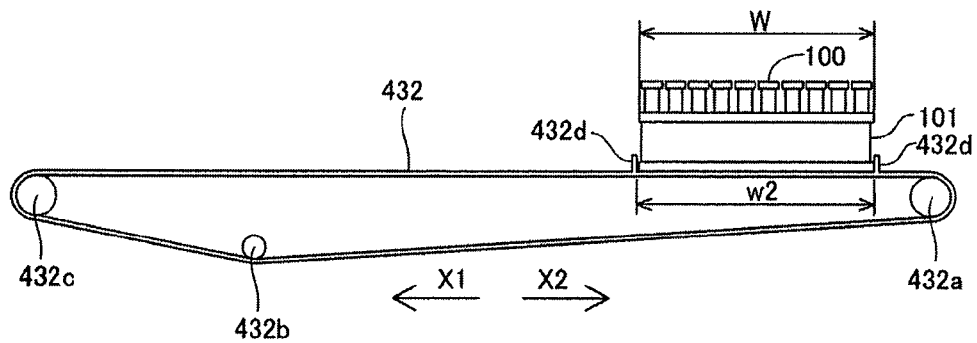
FIG. 8 is a side view illustrating the sample transporting apparatus of the blood analyzer according to the embodiment shown in FIG. 1.

As shown in FIG. 6, the rack transporter 43 has two belts that are a first belt 431 and a second belt 432 capable of moving independently of each other. A width b1 of the first belt 431 in the arrow Y1 direction and a width b2 of the second belt 432 in the arrow Y2 direction are each equal to or smaller than the half of a width B of the rack 101 in the arrow Y1 and Y2 directions. Accordingly, the first belt 431 and the second belt 432 can be arranged in parallel to each other within the width B of the rack 101, so as not to be displaced from the width B when the rack transporter 43 transports the rack 101. Further, as shown in FIGS. 7 and 8, the first belt 431 and the second belt 432 are each formed in an annular shape, and are provided so as to be wound around rollers 431a to 431c and rollers 432a to 432c, respectively. The outer periphery of the first belt 431 has two protrusions 431d formed thereon and the outer periphery of the second belt 432 has two protrusions 432d formed thereon, such that an interval between the protrusions 431d and an interval between the protrusions 432d have an inner width w1 (see FIG. 7) and an inner width w2 (see FIG. 8), respectively, which are both slightly greater (e.g., by approximately 1 mm) than a width W of the rack 101 in the arrow X1 and X2 directions. The first belt 431 is configured to move, when holding the rack 101 between the protrusions 431d, the rack 101 in the arrow X1 or X2 direction as a result of being moved around the rollers 431a to 431c by a stepping motor 431e (see FIG. 3). The stepping motor 431e has an encoder 431f therein. Driving amounts of the stepping motor 431e are each inputted, by the encoder 431f, to a control section 51 of the control apparatus 5 as the number of pulses, and sequentially stored in a ROM 51b or RAM 51c of the control section 51. Also, the second belt 432 is configured to move, when holding the rack 101 between the protrusions 432d, the rack 101 in the arrow X1 or X2 direction as a result of being moved around the rollers 432a to 432c by a stepping motor 432e (see FIG. 3). The stepping motor 432e has an encoder 432f therein. Driving amounts of the stepping motor 432e are each inputted, by the encoder 432f, to the control section 51 as the number of pulses, and sequentially stored in the ROM 51b or RAM 51c. The first belt 431 and the second belt 432 are configured to be able to move racks 101, respectively, and independently of each other. In other words, two racks 101 can be moved independently of each other on the rack transporter 43.

The bar code reader 44 is configured to read the bar code 100b (see FIG. 4) of each sample container 100 that has been transported to the detection position 43c and a bar code 101a affixed to each rack 101. The bar code reader 44 is configured to read the bar code 100b of a target sample container 100 accommodated in a rack 101 when the target sample container 100 is being horizontally rotated by a rotator (not shown) without being removed from the rack 101. Accordingly, even in the case where the bar code 100b affixed to the sample container 100 is located at the opposite side to the bar code reader 44, the bar code 100b can be caused to face the bar code reader 44. Note that the bar code 101a is uniquely assigned to each rack 101, and used for, e.g., managing analysis results of the samples therein.

The presence/absence detection sensor 45 has a curtain-like contact segment, a light emitting element for emitting light, and a light receiving element. The presence/absence detection sensor 45 is configured such that the contact segment 451 is bent when contacted by a detection subject, and as a result, the light emitted from the light emitting element is reflected by the contact segment 451 and then incident on the light receiving element. Accordingly, when a sample container 100 which is accommodated in a rack 101 and which is a detection subject passes below the presence/absence detection sensor 45 (i.e., passes the detection position 43c), the contact segment 451 is bent by the sample container 100. As a result, the presence of the sample container 100 can be detected.

The rack feed-out part 46 is disposed so as to be opposed to the analyzed rack holder 42, with the rack collection position 43d of the rack transporter 43 located therebetween, and is configured to horizontally move in the arrow Y1 direction. The rack feed-out part 46 is configured to, by horizontally moving in the arrow Y1 direction, push a rack 101 disposed at the rack collection position 43d, toward the analyzed rack holder 42 side. Provided near the rack feed-out part 46 is a stepping motor 461. The rack feed-out part 46 transfers, as a result of the stepping motor 461 being driven, the rack 101 to the analyzed rack holder 42.

In the present embodiment, the sample transporting apparatus 4 is configured to maintain, until it is determined for all the samples (blood) in a rack 101 whether or not retesting thereof is necessary, a state where the rack 101 is mounted on the rack transporter 43. To be specific, after all the sample containers 100 have been returned to their predetermined positions in the rack 101, the rack 101 is not moved to the analyzed rack holder 42 but is kept disposed in the rack collection position 43d on the rack transporter 43 until necessity/unnecessity determination for retesting is completed for all the samples. This allows the rack transporter 43 to promptly return, when retesting is necessary, the rack 101 in the upstream transporting direction (i.e., the arrow X2 direction). Accordingly, a sample container 100 of the rack 101 can be promptly disposed at the loading position 43a.

As described below, the sample transporting apparatus 4 is configured to be controlled by the control apparatus 5 so as to feed, after it is determined that retesting is unnecessary for the samples, in a rack (a preceding rack) 101, of the first to sixth sample containers 100 counted from the downstream side of the transporting direction (i.e., counted from the arrow X1 direction side), the next rack (a subsequent rack) 101 from the unanalyzed rack holder 41 to the rack feed-in position 43b on the rack transporter 43. Owing to this configuration, retesting can be performed on the samples of all the sample containers 100 in the preceding rack 101 without returning the subsequent rack 101 to the unanalyzed rack holder 41. Further, the sample processing can be promptly performed for the samples of the subsequent rack 101, following the sample processing on the samples of the preceding rack 101. This consequently prevents stagnation of sample processing, which is caused due to waiting for necessity/unnecessity determination for retesting of the samples of the preceding rack 101.

Figure 9:
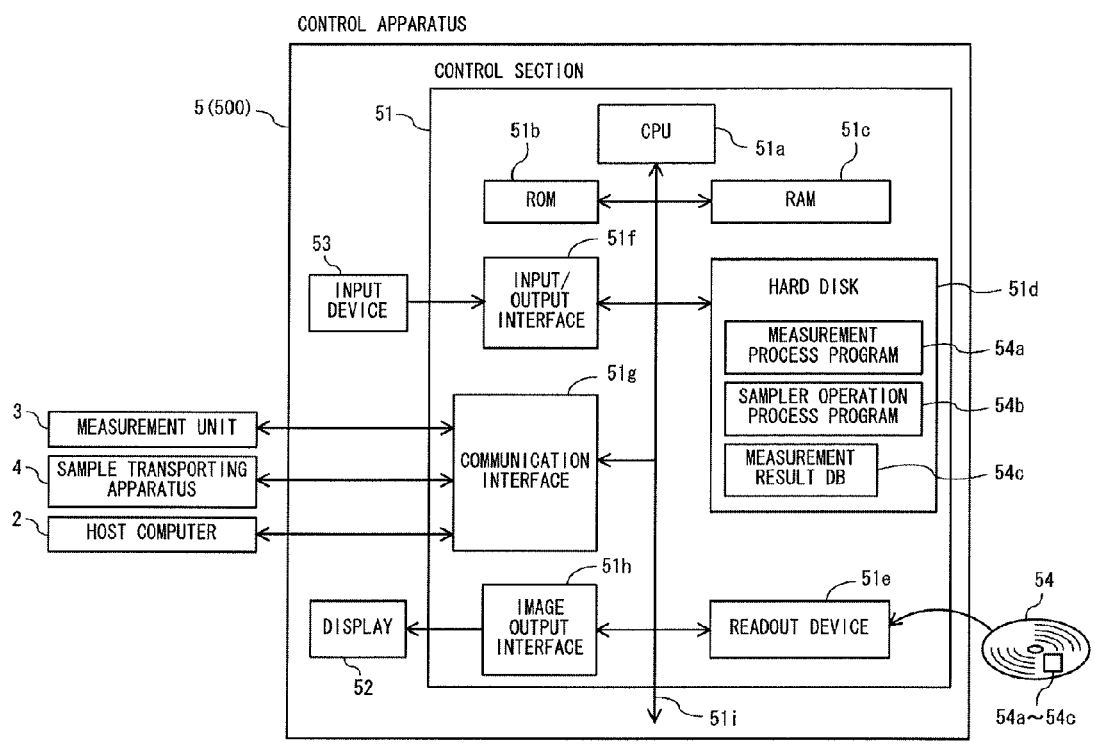
FIG. 9 is a block diagram illustrating a control apparatus of the blood analyzer according to the embodiment shown in FIG. 1.

As shown in FIGS. 1, 2 and 9, the control apparatus 5 is structured as a personal computer (PC) or the like. The control apparatus 5 includes: a control section 51 (see FIG. 9) including a CPU, ROM, RAM and the like; a display 52; and an input device 53. The display 52 is provided so as to display analysis results and the like that are obtained by analyzing digital signal data transmitted from the measurement unit 3.

As shown in FIG. 9, the control apparatus 5 is structured as a computer 500 of which the main components are the control section 51, the display 52, and the input device 53. The main components of the control section 51 are a CPU 51a, a ROM 51b, a RAM 51c, a hard disk 51d, a readout device 51e, an input/output interface 51f, a communication interface 51g, and an image output interface 51h. The CPU 51a, ROM 51b, RAM 51c, hard disk 51d, readout device 51e, input/output interface 51f, communication interface 51g, and the image output interface 51h are connected to each other via a bus 51i.

The CPU 51a is capable of executing computer programs stored in the ROM 51b and computer programs loaded into the RAM 51c. The computer 500 acts as the control apparatus 5 through execution, by the CPU 51a, of application programs 54a and 54b that are described below.

The ROM 51b is structured as a mask ROM, PROM, EPROM, EEPROM or the like, and stores computer programs to be executed by the CPU 51a and stores data to be used by the computer programs.

The RAM 51c is structured as an SRAM, DRAM or the like. The RAM 51c is used for reading computer programs stored in the ROM 51b and the hard disk 51d. The RAM 51c is used as a work area for the CPU 51a when the CPU 51a executes these computer programs.

Installed in the hard disk 51d are: various computer programs to be executed by the CPU 51a, such as an operating system and application programs; and data to be used for executing these computer programs. A measurement process program 54a for the measurement unit 3 and a sampler operation process program 54b for the sample transporting apparatus 4 are also installed in the hard disk 51d. Through the execution of these application programs 54a and 54b by the CPU 51a, operations of respective components of the measurement unit 3 and the sample transporting apparatus 4 are controlled. Further, a measurement result database 54c is also installed in the hard disk 51d.

The readout device 51e is structured as a flexible disc drive, CD-ROM drive, DVD-ROM drive or the like. The readout device 51e is capable of reading computer programs or data, which are stored in a portable storage medium 54. The portable storage medium 54 stores therein the application programs 54a and 54b. The computer 500 is capable of reading the application programs 54a and 54b from the portable storage medium 54 to install the read application programs 54a and 54b in the hard disk 51d.

Note that the application programs 54a and 54b can be provided to the computer 500 not only via the portable storage medium 54, but also from an external device via a telecommunication line (regardless of whether wired or wireless), which external device is communicably connected to the computer 500 by the telecommunication line. For example, the application programs 54a and 54b are stored in a hard disk of a server computer on the Internet. The computer 500 can access the server computer, and download the application programs 54a and 54b from the server computer to install the application programs 54a and 54b in the hard disk 51d.

Also, an operating system that provides a graphical user interface environment, for example, Windows (registered trademark) manufactured and sold by Microsoft Corporation, is installed in the hard disk 51d. In the description below, it is assumed that the application programs 54a and 54b run on the operating system.

For example, the input/output interface 51f is configured as: a serial interface such as USB, IEEE1394 or RS-232C; a parallel interface such as SCSI, IDE or IEEE 1284; or an analogue interface including a D/A converter, A/D converter and the like. The input device 53 is connected to the input/output interface 51f. A user can input data to the computer 500 by using the input device 53.

The communication interface 51g is an Ethernet (registered trademark) interface, for example. The computer 500 is capable of transmitting/receiving data to/from the measurement unit 3, the sample transporting apparatus 4, and the host computer 2 via the communication interface 51g, using a predetermined communication protocol.

The image output interface 51h is connected to the display 52 that is structured with LCD, CRT or the like. Video signals corresponding to image data, which are supplied from the CPU 51a, are outputted to the display 52. The display 52 is configured to display an image (screen) in accordance with the inputted video signals.

The control section 51 having the above configuration is configured to use measurement results transmitted from the measurement unit 3 to analyze components that are analysis subjects, and obtain results of the analysis (red blood count, platelet count, amount of hemoglobin, white blood count, and the like). The control section 51 is also configured to determine, by means of the CPU 51a and based on the measurement results transmitted from the measurement unit 3, whether or not retesting of a sample (blood) is necessary. Further, in the present embodiment, the CPU 51a is configured to, when determining that retesting is necessary for the sample of a sample container 100 held in a rack 101, control the respective components of the sample transporting apparatus 4 so as to perform retesting of the sample in an interrupting manner. To be specific, in the case of retesting, the CPU 51a changes the direction in which the rack 101 is transported by the first belt 431 (see FIG. 6) or the second belt 432 (see FIG. 6), from the downstream transporting direction (the arrow X1 direction) to the upstream transporting direction (the arrow X2 direction). In this manner, the CPU 51a controls the sample transporting apparatus 4, so as to transport the sample container 100, which is the subject of retesting, in the upstream transporting direction (the arrow X2 direction) to the loading position 43a again. Accordingly, the sample container 100, which is the subject of retesting, is directly transported to the loading position 43a from the downstream transporting direction (the arrow X1 direction) side.

The control section 51 stores the number of pulses corresponding to the respective positions on the rack transporter 43 (the presence/absence detection position 43c, the loading position 43a, and the rack collection position 43d). The stored number of pulses is used to control the stepping motor 431e (or 432e) so as to transport a corresponding sample rack 101 to the respective positions on the rack transporter 43. To be more specific, distances from a position, on which a rack origin of a sample rack (downstream direction side head of a sample rack) is located when the sample rack is located at the rack feed-in position 43b (hereinafter, this position may be referred to as an initial position) to the respective positions (the presence/absence detection position 43c, the loading position 43a, and the rack collection position 43d) are each converted into the number of pulses and incorporated in the sampler operation process program 54b stored in the hard disk 51d. The distances are calculated by setting "0" as the number of pulses corresponding to the position of rack origin when the sample rack is located on the initial position. Further, distances from the rack origin to the respective sample holding positions in the sample rack 101 are each converted into the number of pulses and incorporated in the program 54b. Still further, driving amounts of the stepping motor 431e (432e), which correspond to moving distances of a corresponding sample rack from the initial position, are each inputted as the number of pulses by the encoder 431f (432f) to the control section 51, and sequentially stored in the control section 51, as described above. With this configuration, the control section 51 controls the stepping motor 431e (432e) based on the number of pulses, thereby controlling transportation of the corresponding sample rack 101. Hereinafter, transportation of a sample rack 101 by the control section 51 will be described by taking, as an example, a case where retesting has been determined to be necessary.

Figure 21:
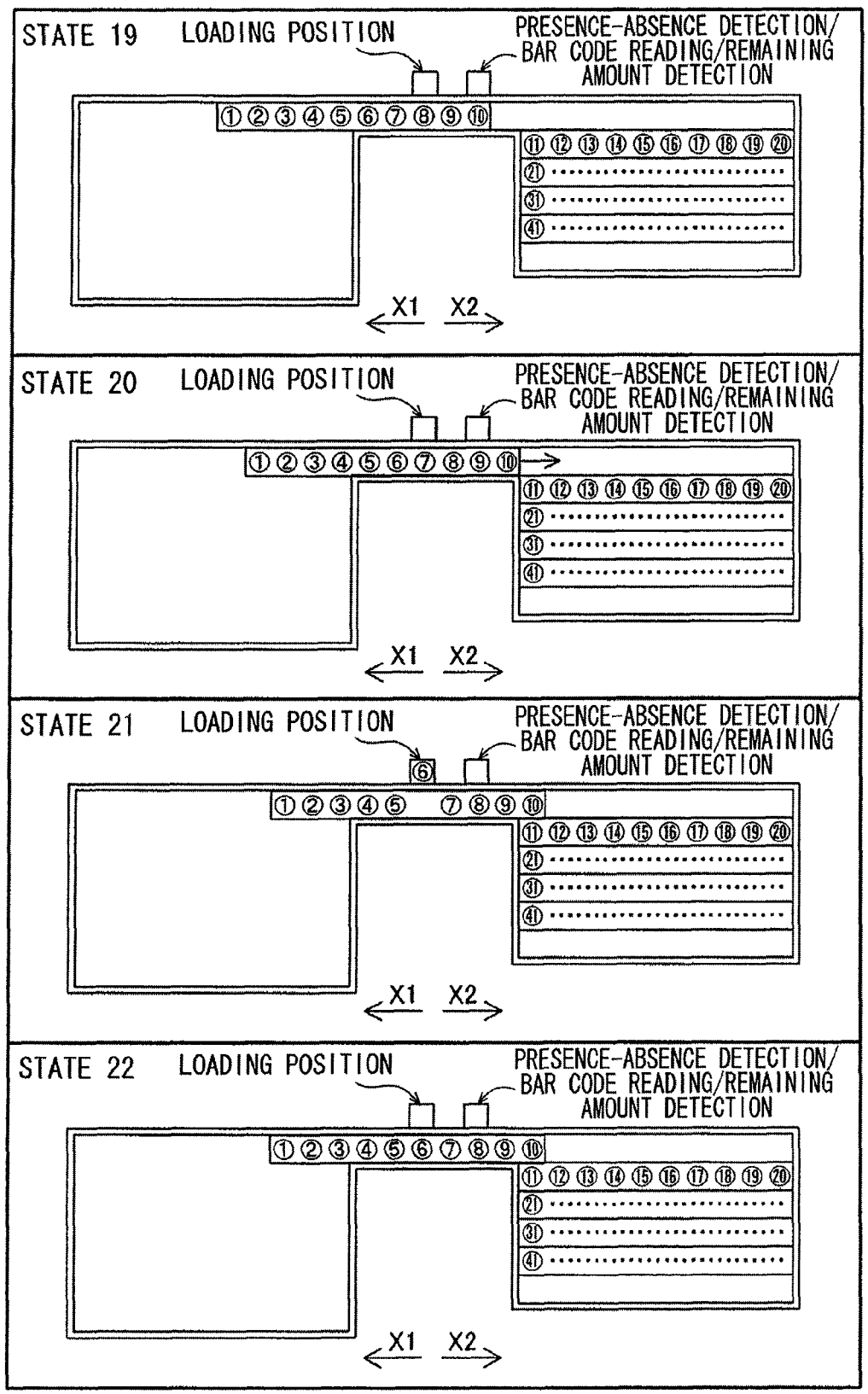
FIG. 21 shows positional relationships among the racks, the sample containers, and the positions in the blood analyzer according to the embodiment shown in FIG. 1.
Figure 22:
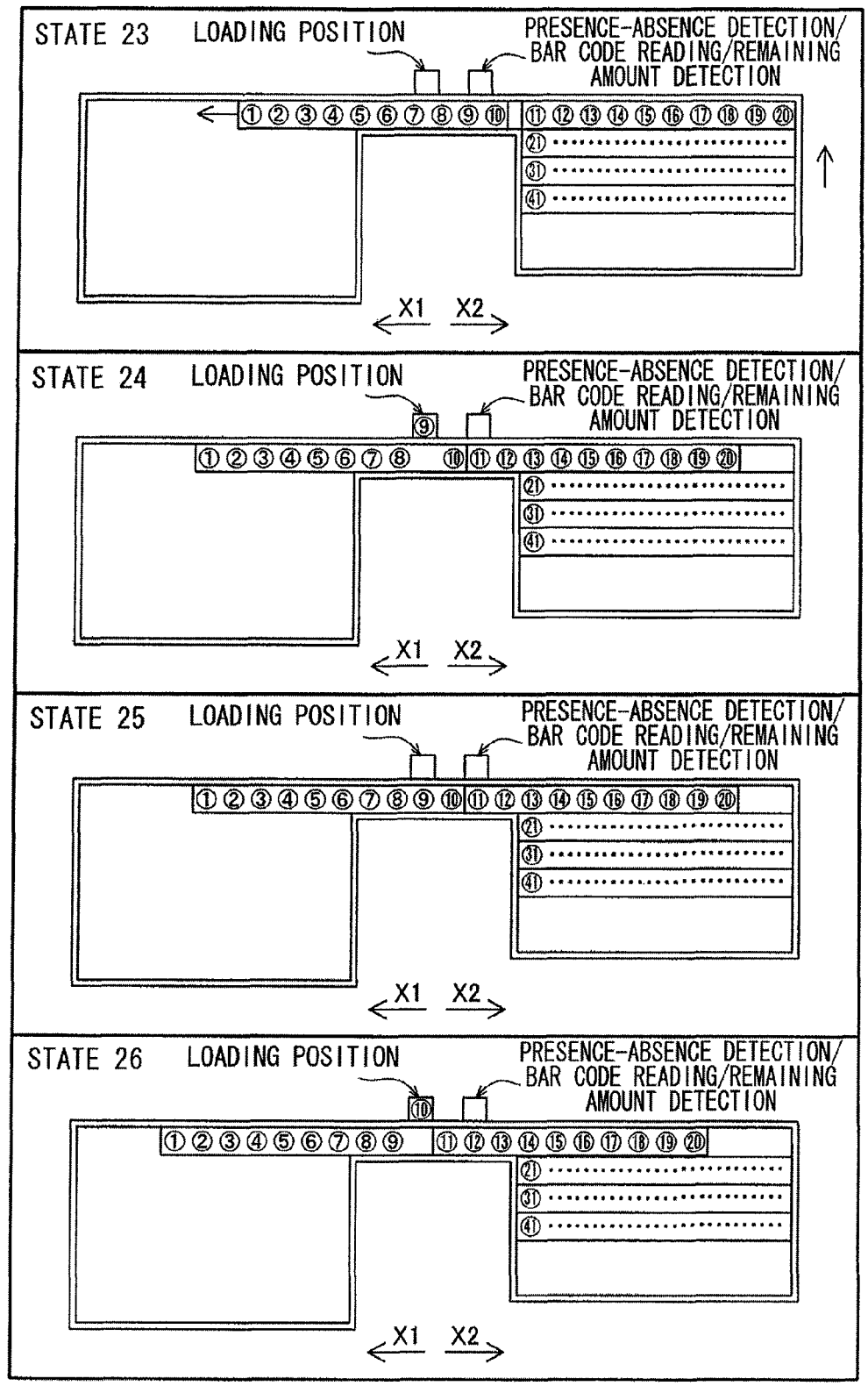
FIG. 22 shows positional relationships among the racks, the sample containers, and the positions in the blood analyzer according to the embodiment shown in FIG. 1.
Figure 23:
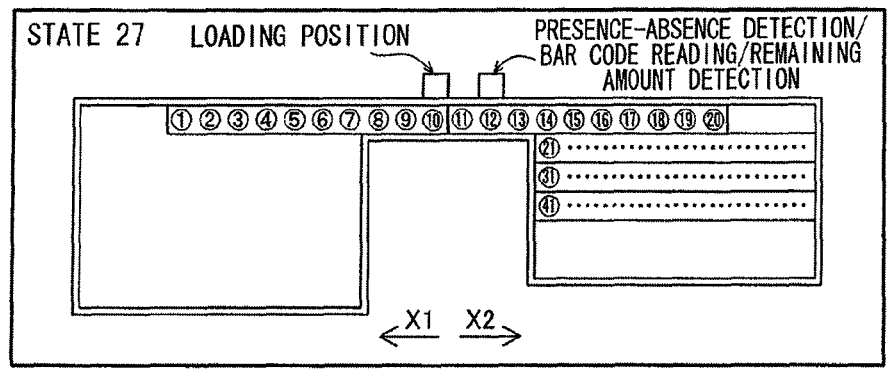
FIG. 23 shows positional relationships among the racks, the sample containers, and the positions in the blood analyzer according to the embodiment shown in FIG. 1.
Figure 24:
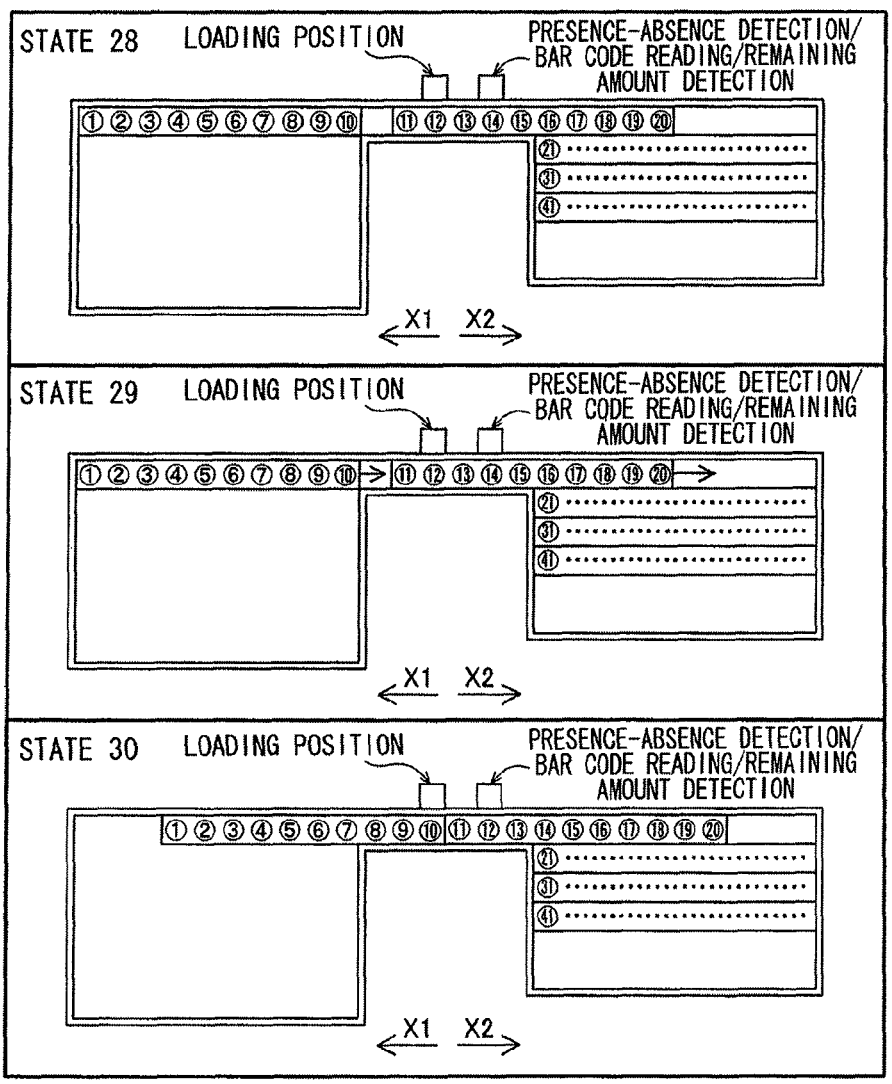
FIG. 24 shows positional relationships among the racks, the sample containers, and the positions in the blood analyzer according to the embodiment shown in FIG. 1.
Figure 25:
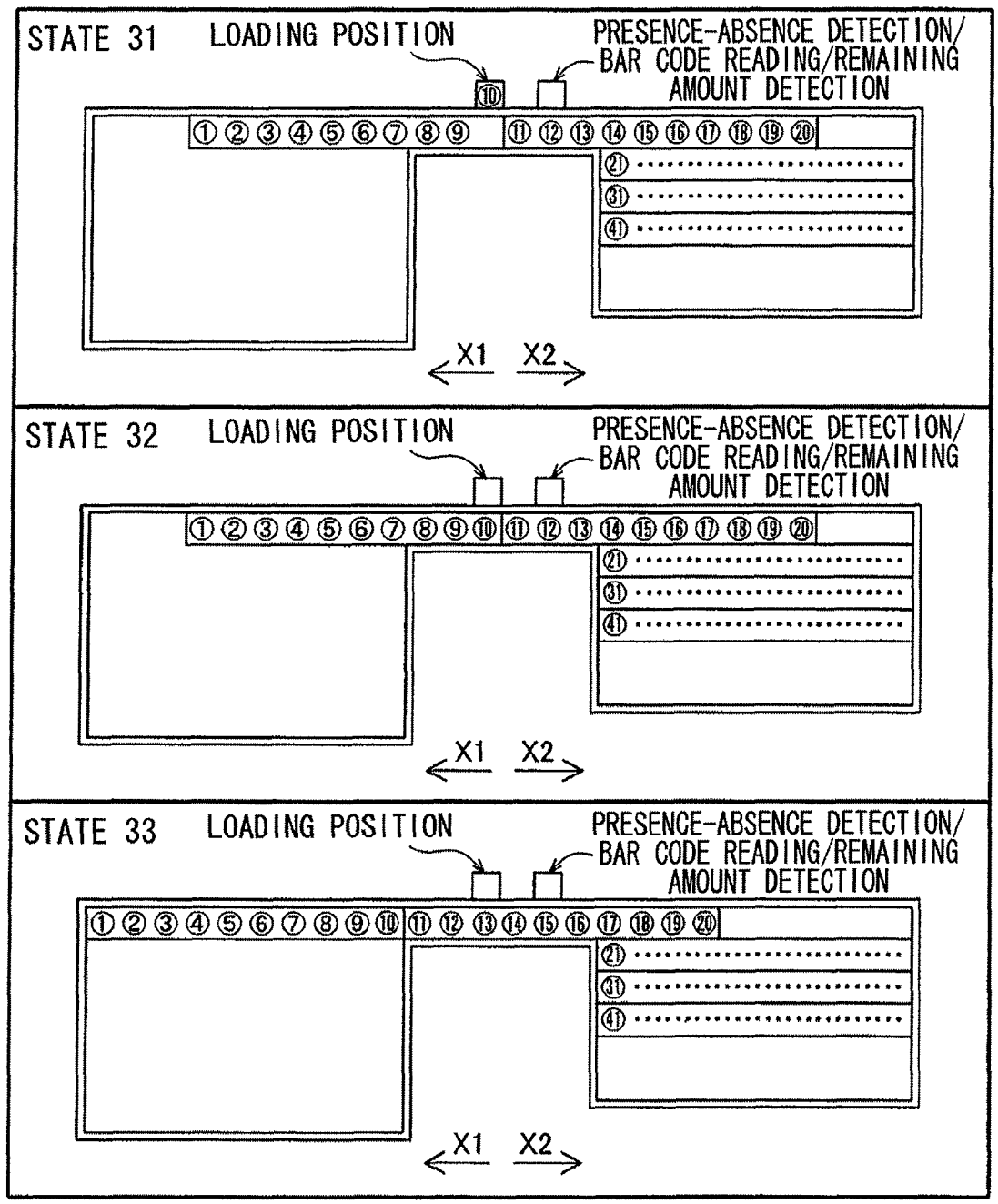
FIG. 25 shows positional relationships among the racks, the sample containers, and the positions in the blood analyzer according to the embodiment shown in FIG. 1.

Described here, as an example, with reference to STATE 19 of FIG. 21 is a case where retesting has been determined to be necessary for the sample of the sixth sample container when the eighth sample container of the sample rack 101 is located at the loading position 43a.

Incorporated in the sampler operation process program 54b are the number of pulses "A" corresponding to a distance from the initial position to the loading position 43a and the number of pulses "B" corresponding to a distance from the rack origin of the sample rack to the position in which the sixth sample is held.

In STATE 19 of FIG. 21, the number of pulses X to be supplied to the stepping motor 431e (or 432e), which is necessary for transporting the sixth sample container to the loading position 43a, is obtained based on an equation shown below when the number of pulses, which corresponds to a moving distance of the sample rack 101 from the initial position to a position indicated in STATE 19, is "C".

$$X = A - (B + C)$$

Accordingly, the CPU 51a reads the number of pulses "C" corresponding to the moving distance of the sample rack 101 from the initial position, the number of pulses "C" having been inputted by the encoder 431f and stored in the control section 51, and then calculates the number of pulses "X" based on the above equation. Note that, if the number of pulses corresponding to a distance from the initial position toward the downstream side of the transporting direction (X1 direction side) is assumed to be plus, and the number of pulses corresponding to a distance from the initial position toward the upstream side (X2 direction side) is assumed to be minus, then the number of pulses X obtained from the above equation is minus.

The CPU 51a controls the stepping motor 431e so as to be driven by the obtained number of pulses X. Here, when the obtained number of pulses X is minus, the CPU 51a controls the stepping motor 431e so as to roll the rollers 431a to 431c in the reverse direction. Accordingly, the direction in which the sample rack 101 is transported by the first belt 431 is switched from the downstream transporting direction (the X1 direction) to the upstream transporting direction (the X2 direction). Then, as shown in STATE 20 of FIG. 19, the sixth sample container is transported toward the loading position 43a, and when the sixth sample container has reached the loading position 43a as shown in STATE 21, the transportation is ceased.

Note that, although the above description has been given, taking a case of retesting as an example, the above processing is applied to all the cases where the sample rack 101 is transported.

Figure 4:
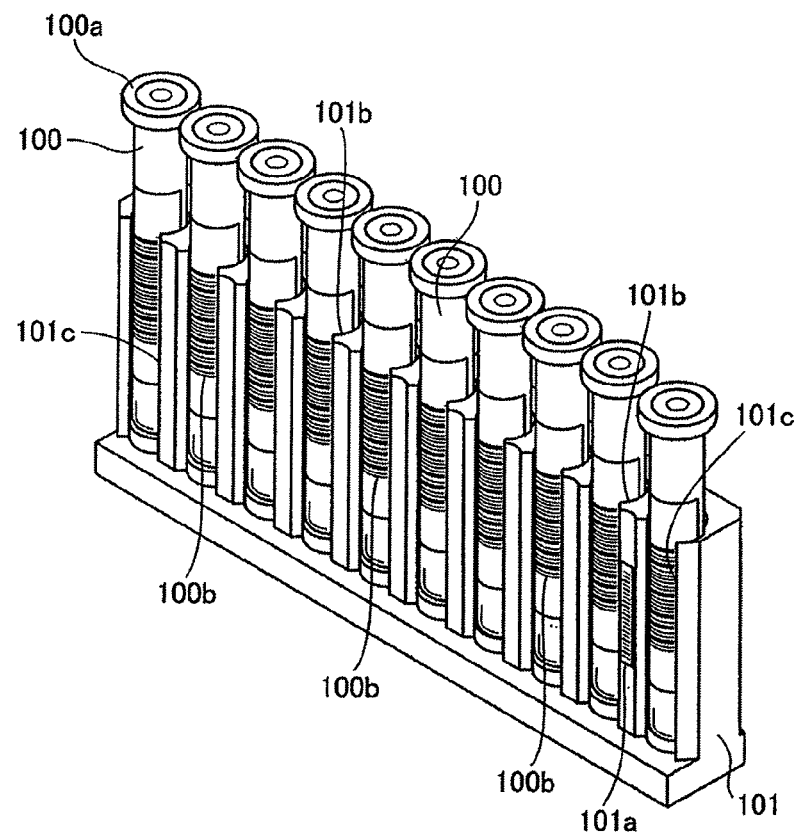
FIG. 4 is a perspective view showing a rack and sample containers of the blood analyzer according to the embodiment shown in FIG. 1.

As shown in FIG. 4, in each rack 101, ten container accommodating portions 101b are formed so as to be able to accommodate ten sample containers 100 in line. Further, the container accommodating portions 101b are each provided with an opening 101c such that the bar code 100b of each sample container 100 accommodated therein can be viewed.

Figure 10:
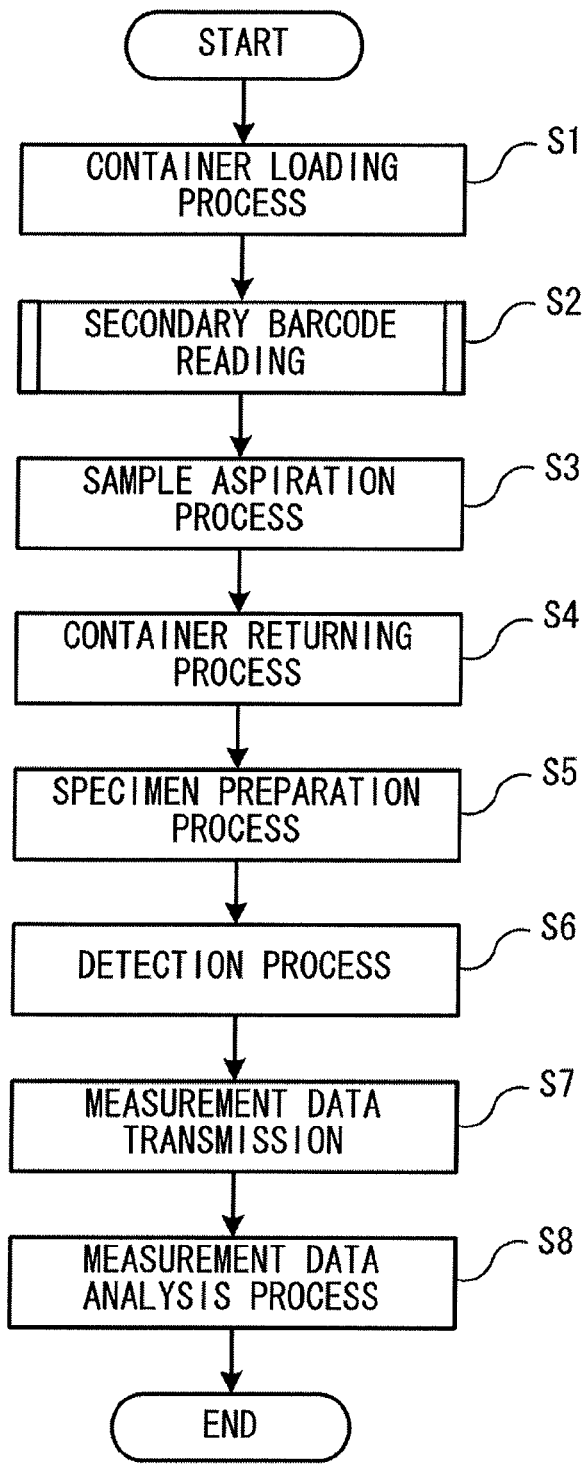
FIG. 10 is a flowchart illustrating operations that are performed, in a measurement process based on a measurement process program, by the blood analyzer according to the embodiment shown in FIG. 1.
Figure 11:
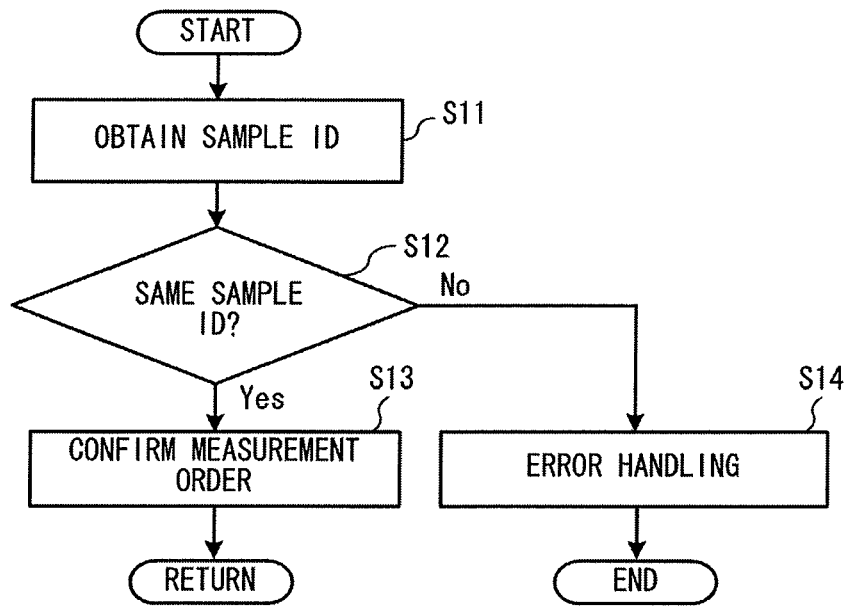
FIG. 11 is a flowchart illustrating a secondary bar code reading process (a subroutine) in the measurement process shown in FIG. 10.

Described next with reference to FIGS. 2, 4, 10, 11, and 15 are operations that are performed, by the blood analyzer 1 according to the present embodiment in a measurement process, based on the measurement process program 54a. The operations in the measurement process as shown in FIG. 10 are performed through control of operations of the respective components (the sample aspirator 31, the specimen preparation section 32, the detector 33, the sample container transporter 35, and the fixedly holding part 36) of the measurement unit 3, the control being performed by the control apparatus 5 (the CPU 51a) of the blood analyzer 1 based on the measurement process program 54a.

First, at step S1, the sample container transporter 35 of the measurement unit 3 obtains, from a rack 101, a sample container 100 that has been transported by the sample transporting apparatus 4 to the loading position 43a, and then loads the obtained sample container 100 into the measurement unit 3. At step S2, the bar code reader 356 performs secondary bar code reading during a period when the loaded sample container 100 is moved by the sample container moving part 355 of the sample container transporter 35 from the sample setting position 710 (see FIG. 2) to the aspirating position 700 (see FIG. 2). Hereinafter, the secondary bar code reading process will be described in detail with reference to FIG. 11.

In the secondary bar code reading process, first, at step S11, the bar code reader 356 reads the bar code 100b affixed to the sample container 100 (see FIG. 4), whereby identification information (sample ID) of the sample contained in the sample container 100 of the read bar code 100b is obtained. Next, at step S12, the CPU 51a of the control apparatus 5 determines whether or not identification information (sample ID), which has been obtained as a result of the bar code reader 44 reading the bar code 100b (see FIG. 4) of the sample container 100 at the detection position 43c (see FIG. 2) of the sample transporting apparatus 4 (primary bar code reading), coincides with the identification information (sample ID) obtained by the bar code reader 356 at step S11. In this manner, it can be determined whether or not the sample to be measured, which has been confirmed based on the identification information (sample ID) obtained by the bar code reader 44 of the sample transporting apparatus 4, has been properly loaded into the measurement unit 3. When the identification information (sample ID) obtained by the bar code reader 356 coincides with the identification information (sample ID) of the sample to be measured, the processing proceeds to step S13, at which, based on the identification information (sample ID), a measurement order (details of an analysis process such as measurement items) is confirmed, which is obtained during a below-described order inquiry process (see FIG. 15). Then, the processing proceeds to processes at step S3 and the subsequent steps of FIG. 10.

Whereas, when the identification information (sample ID) obtained by the bar code reader 356 at step S12 does not coincide with the identification information (sample ID) of the sample to be measured, the processing proceeds to step S14, at which the CPU 51a of the control apparatus 5 performs error handling. To be specific, the sample container 100, which has been loaded into the measurement unit 3 by the sample container transporter 35, is returned to the corresponding rack 101. Then, a user is notified, by a message displayed on the display 52 of the control apparatus 5, that the identification information (sample ID) obtained by the bar code reader 356 does not coincide with the identification information (sample ID) of the sample to be measured. Thereafter, the processing by the blood analyzer 1 is terminated. With the above, the secondary bar code reading process ends.

When the secondary bar code reading ends, the sample aspirator 31 aspirates the sample, at step S3 of FIG. 10, from the sample container 100 having been transported to the aspirating position 700 (see FIG. 2). Then, at step S4, the sample container 100, from which the sample has been aspirated, is moved by the sample container transporter 35 to the outside of the measurement unit 3, and returned to a container accommodating portion 101b of the rack 101, which is the original storing position of the sample container 100. At step S5, a detection specimen is prepared from the aspirated sample by the specimen preparation section 32. At step S6, the detector 33 detects, from the detection specimen, components that are analysis subjects. Then, at step S7, measurement data is transmitted from the measurement unit 3 to the control apparatus 5. Thereafter, at step S8, the control section 51 analyzes, based on the measurement data transmitted from the measurement unit 3, the components that are analysis subjects. In the measurement data analysis process at step S8, the CPU 51a of the control apparatus 5 determines, based on measurement results of the sample which are obtained from the measurement unit 3, whether or not retesting of the sample is necessary (necessity/unnecessity determination for retesting). Here, when retesting of the sample is determined to be necessary, the CPU 51a generates analysis results that contain a retest flag for the sample, and the sample becomes a subject of below-described interruption retesting. Whereas, when retesting of the sample is determined to be unnecessary, the CPU 51a generates analysis results that do not contain a retest flag. Accordingly, the testing process for the sample ends. Note that, in the present embodiment, retesting is not performed again on a sample for which retesting has already been performed (i.e., retesting is not performed twice on the same sample). That is, in the necessity/unnecessity determination for retesting, which is performed by the control apparatus 5 (the CPU 51a), retesting is determined to be unnecessary for the sample on which retesting has already been performed. At step S8, the analysis of the sample is completed, and the operations of the single measurement process performed on the sample are ended.

Figure 12:
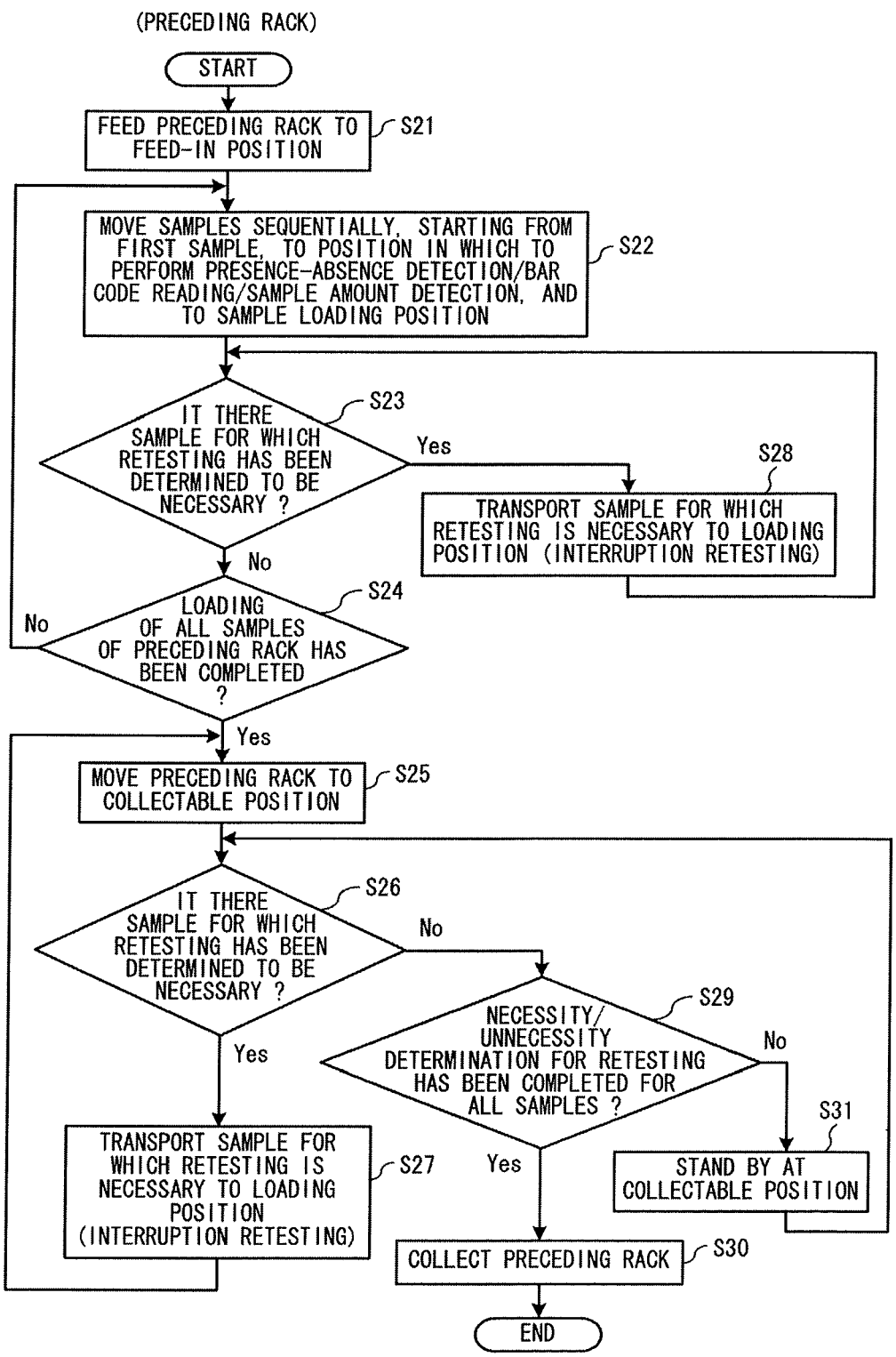
FIG. 12 is a flowchart illustrating a process of transporting a preceding rack, which is performed based on a sampler operation process program by the blood analyzer according to the embodiment shown in FIG. 1.

Described next with reference to FIGS. 2, 10 to 12, and 15 to 25 is a process of transporting a preceding rack 101, which is performed, based on the sampler operation process program 54b, by the control apparatus 5 (the CPU 51a) of the blood analyzer 1 according to the present embodiment. The transporting process of the preceding rack 101, which is shown in FIG. 12, is performed through control of operations of the respective components (the stepping motor 413 of the unanalyzed rack holder 41, the stepping motor 431e and the stepping motor 432e of the rack transporter 43, the stepping motor 461 for driving the rack feed-out part 46, and the like) of the sample transporting apparatus 4, the control being performed by the control apparatus 5 (the CPU 51a) of the blood analyzer 1 based on the sampler operation process program 54b. Here, referred to as a preceding rack 101 is a rack 101 that has been fed from the unanalyzed rack holder 41 to the rack feed-in position 43b on the rack transporter 43 in advance of another rack, and referred to as a subsequent rack 101 is a rack 101 that has been fed so as to follow the preceding rack 101 already present on the rack transporter 43. Note that the sampler operation process program 54b of the blood analyzer 1 is executed in parallel with the aforementioned measurement process program 54a.

First, at step S21 of FIG. 12, the sample transporting apparatus 4 is initialized. Here, the protrusions 431d of the first belt 431 are moved to predetermined positions. These positions are set as original positions of the first belt 431. The two protrusions 431d are moved to positions corresponding to the rack feed-in position 43b, and then the preceding rack 101 is fed between the two protrusions 431d of the first belt 431. In this manner, the preceding rack 101 is disposed at the rack feed-in position 43b as shown in STATE 1 of FIG. 16.

Next, at step S22, the preceding rack 101 is transversely fed in the downstream transporting direction (the arrow X1 direction). Accordingly, presence/absence detection of a sample container 100, reading of the bar code 100b (primary bar code reading) of the sample container 100, and sample amount detection of the sample contained in the sample container 100, are performed at the detection position 43c, sequentially for the sample containers 100 of the preceding rack 101, starting from the first sample container 100. The hand part 351 loads the samples of these sample containers 100 into the measurement unit 3 at the loading position 43a. Specifically, as shown in STATE 2 and STATE 3 of FIG. 16, the preceding rack 101 is transversely fed in the downstream transporting direction (the arrow X1 direction). As a result, the first sample container 100 is transported to the detection position 43c and then the predetermined processes are performed thereon. Thereafter, the preceding rack 101 is further transversely fed in the downstream transporting direction (the arrow X1 direction). As a result, as shown in STATE 4 of FIG. 16, the second sample container 100 is transported to the detection position 43c, and then the predetermined processes are performed thereon. To be specific, at the detection position 43c, the bar code reader 44 (see FIG. 2) reads the bar code 100b of each sample container 100 (primary bar code reading) sequentially. Accordingly, the control apparatus 5 (the CPU 51a) performs the order inquiry process in parallel with the transporting process of the rack 101. Hereinafter, the order inquiry process performed by the control apparatus 5 (the CPU 51a) will be described with reference to FIG. 15.

Figure 15:
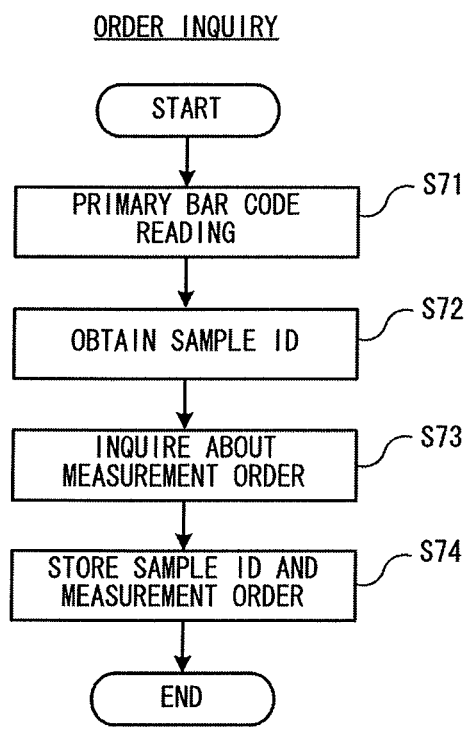
FIG. 15 is a flowchart illustrating an order inquiry process that is performed following primary bar code reading in the transporting process of the preceding rack shown in FIG. 12 or in the transporting process of the subsequent rack shown in FIG. 13.
Figure 16:
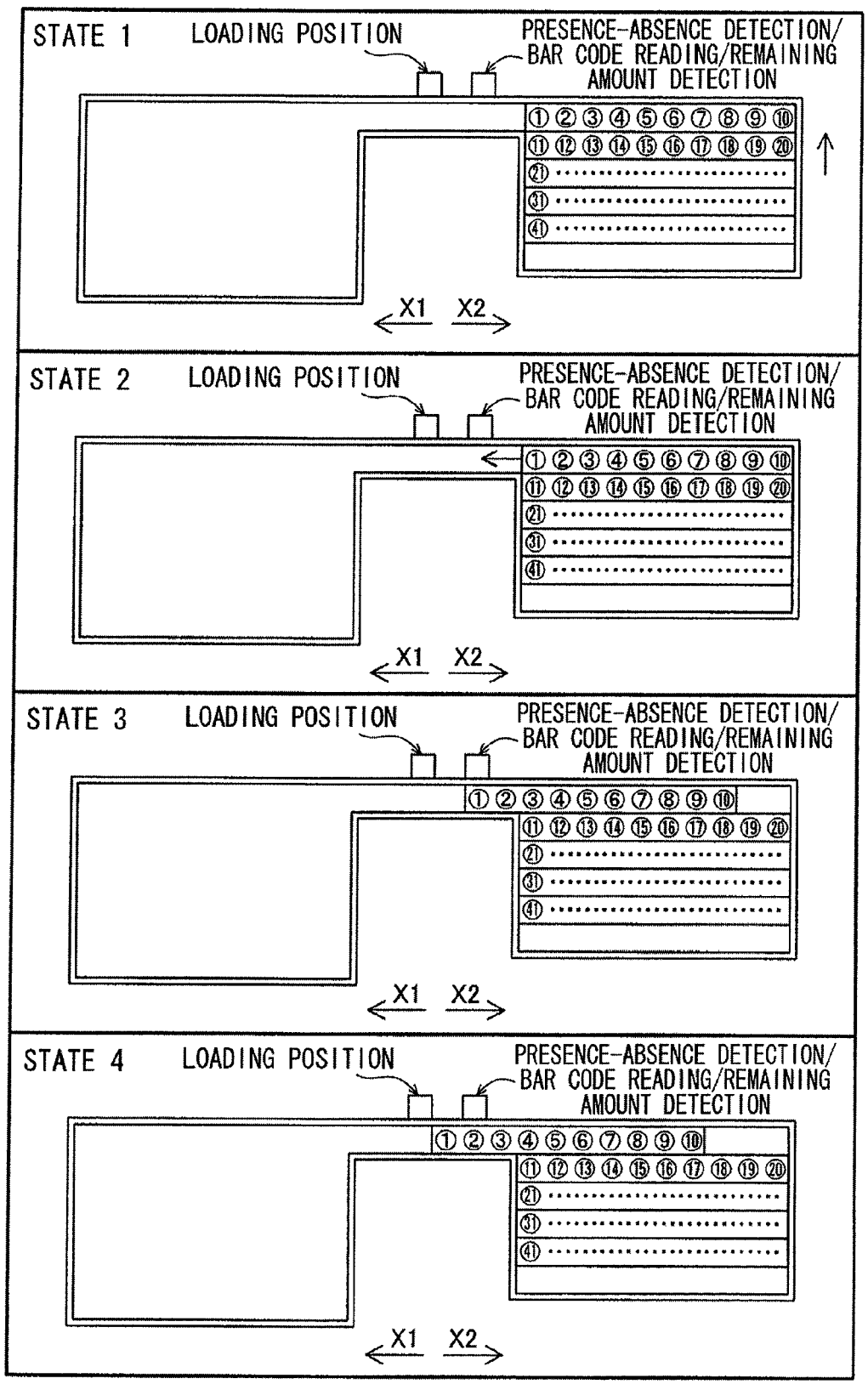
FIG. 16 shows positional relationships among racks, sample containers, and positions in the blood analyzer according to the embodiment shown in FIG. 1.

As shown in FIG. 15, in the order inquiry process, at step S71, the bar code 100b of a sample container 100 disposed at the detection position 43c is read by the bar code reader 44 (primary bar code reading). Next, at step S72, the read data is transmitted from the bar code reader 44 to the control apparatus 5. The CPU 51a of the control apparatus 5 obtains identification information (sample ID) of the sample contained in the sample container 100 of the read bar code 100b. Then, at step S73, the CPU 51a inquires of the host computer 2 about a measurement order (details of an analysis process to be performed by the measurement unit 3, such as measurement items) corresponding to the obtained identification information (sample ID) of the sample. Then, at step S74, the CPU 51a obtains, from the host computer 2, the measurement order corresponding to the obtained identification information (sample ID) of the sample. Then, the identification information (sample ID) and the measurement order corresponding thereto are stored in the RAM 51c of the control apparatus 5. Note that the secondary bar code reading process (see FIG. 11) shown in step S2 of FIG. 10 uses the identification information (sample ID) and the measurement order corresponding to the sample ID, which are stored in the RAM 51c in the order inquiry process. With the above, the order inquiry process ends. Each time the primary bar code reading is performed on a sample container 100, identification information (sample ID) of the sample container 100 and a measurement order corresponding thereto are obtained by the control apparatus 5.

Subsequently, at step S22 of FIG. 12, the first sample container 100 is transported to the loading position 43a and loaded into the measurement unit 3 as shown in STATE 5 of FIG. 17 (see step S1 of FIG. 10). Here, the third sample container 100 has been transported to the detection position 43c. Accordingly, the predetermined processes are performed on the third sample container 100. Thereafter, as shown in STATE 6 of FIG. 17, the first sample container 100, for which the processes performed within the measurement unit 3 have been completed, is returned to a container accommodating portion 101b of the preceding rack 101, which is the original storing position of the first sample container 100 (see step S4 of FIG. 10). Subsequently, the second sample container 100 is transported to the loading position 43a, and the same processes as those performed on the first sample container 100 are performed on the second sample container 100. Here, since the measurement unit 3 performs the processes of steps S5 and S6 of FIG. 10, the second sample container 100 is loaded into the measurement unit 3 when a predetermined time (approximately 36 seconds) has elapsed after the first sample container 100 has been loaded into the measurement unit 3. Thereafter, in the same manner as described above, the sample containers 100 are sequentially loaded into the measurement unit 3 at predetermined intervals (approximately every 36 seconds), and the predetermined processes are performed on these sample containers 100.

At step S23, the CPU 51a sequentially determines, for the loaded samples, presence/absence of a sample for which retesting has been determined to be necessary (see step S8 of FIG. 10). To be specific, when a predetermined time (75 seconds) has elapsed after a sample container 100 has been loaded into the measurement unit 3, the control apparatus 5 (the CPU 51a) determines (see step S8 of FIG. 10) whether or not retesting is necessary for the sample contained in the sample container 100. Accordingly, whether or not retesting is necessary for the sample of a particular sample container 100 is determined while a sample container 100 that is two sample containers down from said particular sample container 100 in the loading sequence is loaded within the measurement unit 3. For example, whether or not retesting is necessary for the sample of the first sample container 100 is determined while the third sample container 100 is loaded within the measurement unit 3; and whether or not retesting is necessary for the sample of the second sample container 100 is determined while the fourth sample container 100 is loaded within the measurement unit 3. In the case where a sample for which retesting is necessary is not present (i.e., a case where analysis results containing a retest flag do not exist), it is determined at step S24 whether or not the loading of all the samples of the preceding rack 101 into the measurement unit 3 has been completed. When the loading of all the samples has not been completed, the processing returns to step S22, at which the transporting of sample containers 100 to the loading position 43a (i.e., the loading into the measurement unit 3) continues. Whereas, when the loading of all the samples has been completed, the preceding rack 101 is, after the tenth (the last) sample container 100 has been returned to the preceding rack 101, transversely fed to the rack collection position 43d (a collectable position) at step S25 as shown in STATE 10 to STATE 12 of FIG. 18 and STATE 13 of FIG. 19.

When it is determined at step S23 that a sample for which retesting has been determined to be necessary is present in the preceding rack 101 (when analysis results containing a retest flag have been generated), the CPU 51a, at step S28, changes the transporting direction of the preceding rack 101 from the downstream transporting direction (the arrow X1 direction) to the upstream transporting direction (the arrow X2 direction), and controls the sample transporting apparatus 4 so as to transport again the sample (the sample container 100), for which retesting is necessary, in the upstream transporting direction (the arrow X2 direction) to the loading position 43a. Then, interruption retesting is performed as a result of the sample, which is the subject of retesting, being loaded into the measurement unit 3 in the container loading process shown in step S1 of FIG. 10. To be specific, when it is determined in STATE 7 shown in FIG. 17 that retesting of the sixth sample is necessary, the sixth sample container 100 is transported in the upstream transporting direction (the arrow X2 direction) directly to the loading position 43a after the eighth sample container 100 has been returned to the preceding rack 101, as shown in STATE 19 and STATE 20 of FIG. 21. Then, as shown in STATE 21 and STATE 22 of FIG. 21, the sixth sample container 100 is loaded into the measurement unit 3 and retesting is performed thereon, and returned to a container accommodating portion 101b of the preceding rack 101, which is the original storing position of the sixth sample container 100. That is, retesting of the sixth sample is performed after testing of the eighth sample and before testing of the ninth sample.

When the interruption retesting at step S28 ends, the processing returns to step S23, at which the CPU 51a determines, for the loaded samples, presence or absence of a sample for which retesting has been determined to be necessary. If a result of the necessity/unnecessity determination for retesting, which is obtained during the interruption retesting, indicates presence of a sample for which retesting has been determined to be necessary (e.g., a case where retesting of the seventh sample is determined to be necessary during the retesting of the sixth sample), the processing proceeds to step S28, at which interruption retesting is performed on the sample (the seventh sample) for which retesting has newly been determined to be necessary. Whereas, if a sample for which retesting has been determined to be necessary is not present, the transporting direction is changed from the upstream transporting direction (the arrow X2 direction) to the downstream transporting direction (the arrow X1 direction), and the ninth and tenth sample containers 100 that have not been loaded are sequentially transported to the loading position 43a and loaded into the measurement unit 3, as shown in STATE 23 to STATE 26 of FIG. 22 and STATE 27 of FIG. 23. In practice, the above steps S22 to S24 and S28 are performed in parallel.

Figure 19:
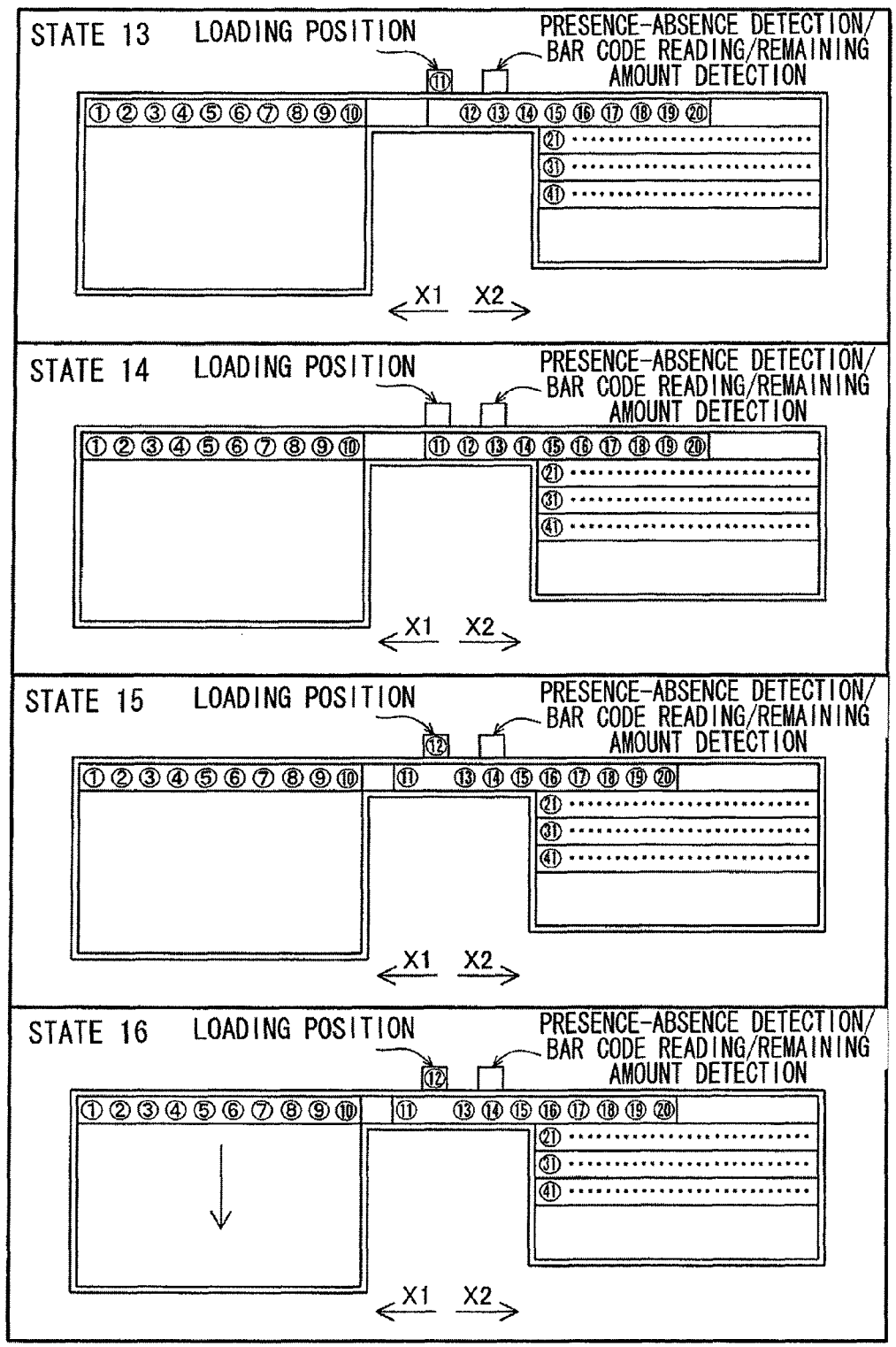
FIG. 19 shows positional relationships among the racks, the sample containers, and the positions in the blood analyzer according to the embodiment shown in FIG. 1.
Figure 20:
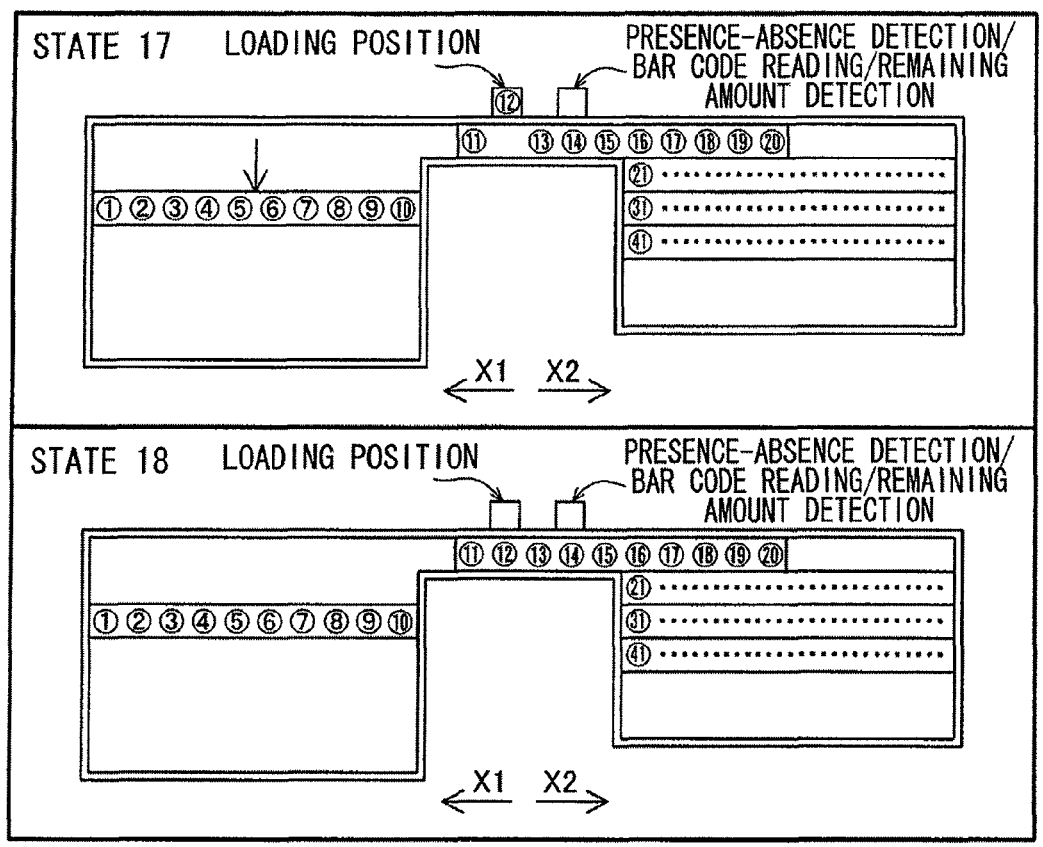
FIG. 20 shows positional relationships among the racks, the sample containers, and the positions in the blood analyzer according to the embodiment shown in FIG. 1.

At step S26, it is determined, when the preceding rack 101 is disposed at the rack collection position 43d (the collectable position) as shown in STATE 13 to STATE 15 of FIG. 19, whether or not the samples in the preceding rack 101 include a sample for which retesting has been determined to be necessary. To be specific, when the preceding rack 101 is disposed at the rack collection position 43d, necessity/unnecessity determination for retesting has already been completed for the first to eighth sample, and necessity/unnecessity determination for retesting is waited to be performed on the ninth and tenth samples. Then, if it is determined that retesting is necessary for the ninth or tenth sample, the CPU 51a controls, at step S27, the sample transporting apparatus 4 so as to transport again the sample (the sample container 100), for which retesting is necessary, in the upstream transporting direction (the arrow X2 direction) to the loading position 43a. Then, the sample to be retested is loaded into the measurement unit 3 in the container loading process shown in step S1 of FIG. 10, and interruption retesting is performed, accordingly. To be specific, when it is determined that retesting is necessary for the tenth sample of the preceding rack 101, the preceding rack 101 is, after the second sample container 100 of the subsequent rack 101 (the twelfth sample container counted from the first sample container of the preceding rack 101) has been returned from the measurement unit 3 to the subsequent rack 101, transported in the upstream transporting direction (the arrow X2 direction) together with the subsequent rack 101 as shown in STATE 28 to STATE 30 of FIG. 24, so as to reach the loading position 43a such that the tenth sample container 100 of the preceding rack 101 is disposed at the loading position 43a. Then, after the tenth sample container 100 of the preceding rack 101 is loaded into, and retested by, the measurement unit 3 and returned to the preceding rack 101, the preceding rack 101 is transversely fed to the rack collection position 43d, as shown in STATE 31 to STATE 33 of FIG. 25.

On the other hand, when no sample in the preceding rack 101 requires retesting, it is determined at step S29 whether or not necessity/unnecessity determination for retesting has been completed for all the samples of the preceding rack 101. When necessity/unnecessity determination has been completed for all the samples, the rack feed-out part 46 collects the preceding rack 101 located at the rack collection position 43d into the analyzed rack holder 42 and the transporting process of the preceding rack 101 ends, accordingly, at step S30 as shown in STATE 16 of FIG. 19 and STATE 17 of FIG. 20. Whereas, when necessity/unnecessity determination for retesting has not been completed for all the samples of the preceding rack 101, the standby state of the preceding rack 101 at the rack collection position 43d (the collectable position) is maintained at step S31. In practice, the above steps S25 to S27, S29, and S31 are performed in parallel.

Figure 13:
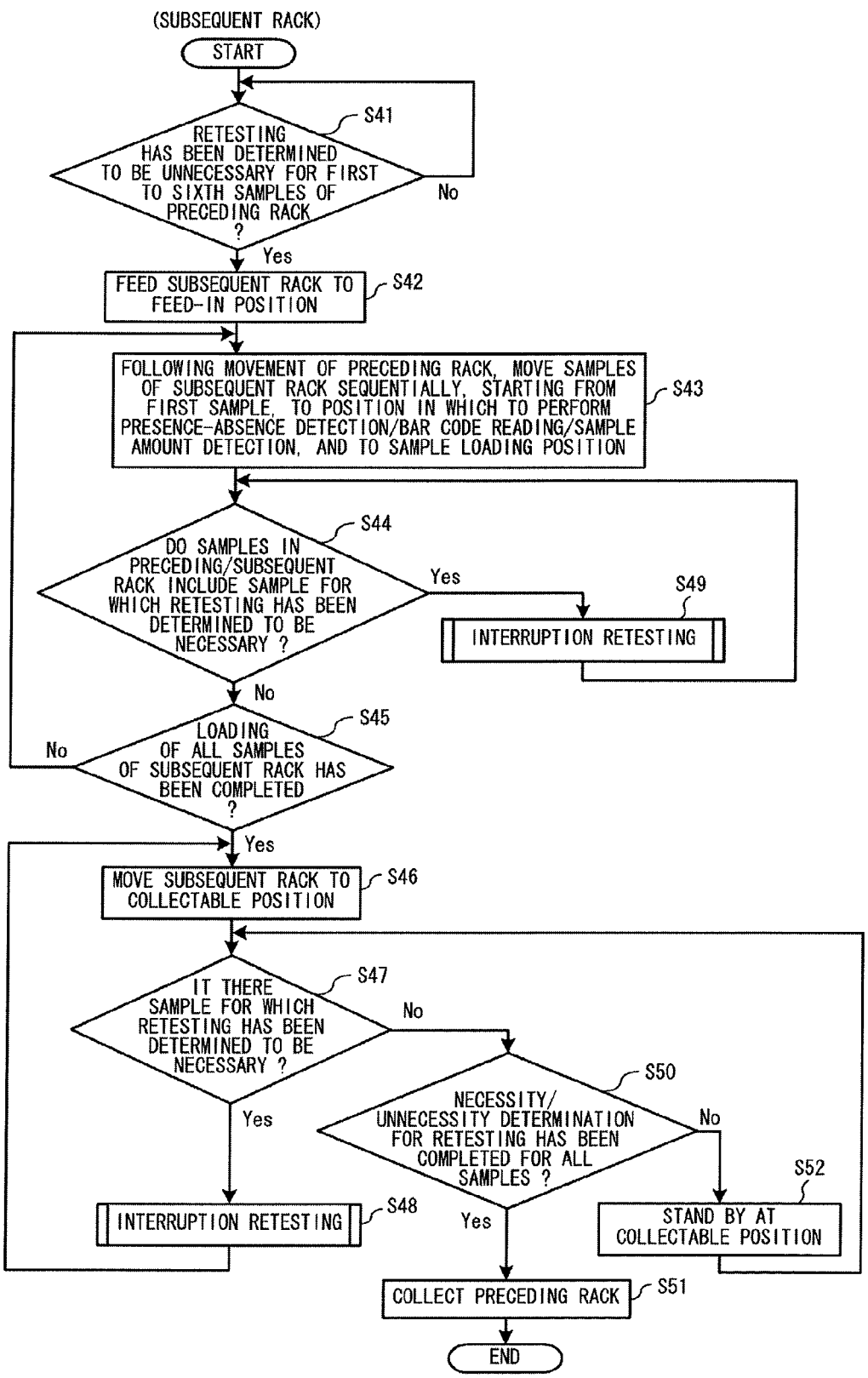
FIG. 13 is a flowchart illustrating a process of transporting a subsequent rack, which is performed based on the sampler operation process program by the blood analyzer according to the embodiment shown in FIG. 1.
Figure 14:
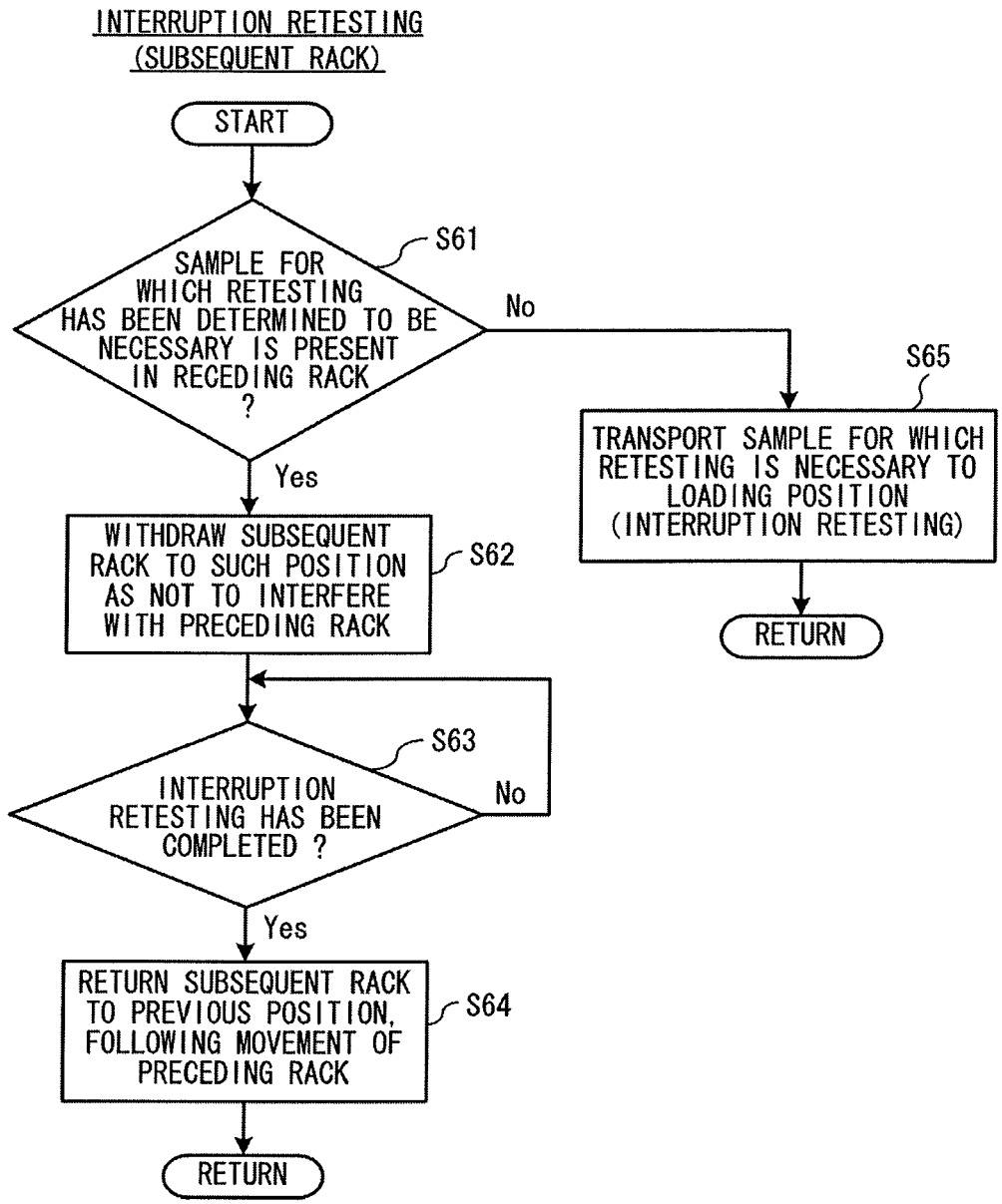
FIG. 14 is a flowchart illustrating an interruption retesting process (a subroutine) in the transporting process of the subsequent rack shown in FIG. 13.

Described next with reference to FIGS. 2, 10 to 15, 17 to 20, and 24 is a process of transporting a subsequent rack 101, which is performed, based on the sampler operation process program 54b, by the control apparatus 5 (the CPU 51a) of the blood analyzer 1 according to the present embodiment. The transporting process of the subsequent rack 101 as shown in FIGS. 13 and 14 is performed through control of operations of the respective components (the stepping motor 413 of the unanalyzed rack holder 41, the stepping motor 431e and the stepping motor 432e of the rack transporter 43, and the stepping motor 461 for driving the rack feed-out part 46) of the sample transporting apparatus 4, the control being performed by the control apparatus 5 (the CPU 51a) of the blood analyzer 1 based on the sampler operation process program.

First, at step S41 of FIG. 13, the CPU 51a determines whether or not retesting has been determined to be unnecessary for the first to sixth samples of the preceding rack 101 (all the samples held in container accommodating portions 101b located farther, in the downstream transporting direction (the arrow X1 direction), than the seventh sample). This determination is repeated until retesting is determined to be unnecessary for the first to sixth samples. Note that, as described above, retesting is determined to be unnecessary for a sample for which retesting has once been determined to be necessary and the retesting has already been performed (i.e., a sample that has already been loaded into the measurement unit 3 twice). In other words, retesting is not performed on a sample that has already been retested. When retesting has been determined to be unnecessary for the first to sixth samples of the preceding rack 101, the rack feed-in part 411 (see FIG. 2) feeds, at step S42, a subsequent rack 101 to the rack feed-in position 43b from the unanalyzed rack holder 41. To be specific, whether or not retesting is necessary for the sixth sample of the preceding rack 101 is determined (see step S8 of FIG. 10) while the eighth sample container 100 of the preceding rack 101 is loaded within the measurement unit 3 as shown in STATE 7 of FIG. 17. Then, when retesting has been determined to be unnecessary for the sixth sample, the subsequent rack 101 is fed to the rack feed-in position 43b as shown in STATE 8 of FIG. 17. Thereafter, at step S43, the subsequent rack 101 is transversely fed in the downstream transporting direction (the arrow X1 direction), following the movement of the preceding rack 101. Accordingly, the sample containers 100 of the subsequent rack 101 are sequentially transported, from the first sample container 100, to the detection position 43c and the loading position 43a. Note that, similarly to the samples of the preceding rack 101, the order inquiry process (see FIG. 15) following the primary bar code reading is performed at the detection position 43c, and the measurement process by the measurement unit 3 is performed at the loading position 43a (see FIGS. 10 and 11). To be specific, as shown in STATE 9 to STATE 12 of FIG. 18, the samples of the subsequent rack 101 are sequentially transported to the detection position 43c and the loading position 43a, in parallel with the processing of the ninth and tenth samples of the preceding rack 101. Then, as shown in STATE 13 to STATE 15 of FIG. 19, the first and second samples of the subsequent rack 101 are sequentially loaded into the measurement unit 3 while the preceding rack 101 is standing by at the rack collection position 43d.

In parallel with the processing at the above step S43, it is determined at step S44 whether or not a sample for which retesting is necessary is present in the preceding rack 101 or in the subsequent rack 101. When the samples of both the racks do not require retesting, it is determined at step S45 whether or not loading of all the samples of the subsequent rack 101 into the measurement unit 3 has been completed. When the loading of all the samples of the subsequent rack 101 has not been completed, the processing returns to step S43. Whereas, when the loading has been completed, the processing proceeds to step S46. Note that the determination, performed at step S44, as to whether or not retesting is necessary for the samples of the preceding rack 101, is the same process as that performed at step S26 of FIG. 12. In other words, when retesting is necessary for a sample of the preceding rack 101, interruption retesting of the sample is performed at step S27 of FIG. 12. Whereas, when no sample in the preceding rack 101 requires retesting, the processing proceeds to step S30 through step S29 of FIG. 12. Then, as shown in STATE 17 of FIG. 20, the preceding rack 101 is collected into the analyzed rack holder 42. After the preceding rack 101 has been collected into the analyzed rack holder 42, the processing on the samples of the subsequent rack 101 continues as shown in STATE 18 of FIG. 20.

When it is determined at step S44 that retesting of one of the samples is necessary (i.e., when analysis results containing a retest flag are generated), a process of interruption retesting is performed at step S49. Hereinafter, interruption retesting performed for the subsequent rack 101 will be described with reference to FIG. 14. In the interruption retesting for the subsequent rack 101, first, at step S61, the CPU 51a of the control apparatus 5 determines whether or not a sample for which retesting has been determined to be necessary is present in the preceding rack 101. When retesting is performed on a sample of the preceding rack 101 (i.e., a case of interruption retesting at step S27 or S28 of FIG. 12), the processing proceeds to step S62, at which the subsequent rack 101 is withdrawn to such a position as not to interfere with the preceding rack 101. For example, when the tenth sample of the preceding rack 101 is retested, the subsequent rack 101 is withdrawn as shown in STATE 30 of FIG. 24, such that the first sample of the subsequent rack 101 (i.e., the eleventh sample) is disposed at a position that is farther, in the upstream transporting direction (the arrow X2 direction) by one sample container 100, than the loading position 43a. Then, it is determined at step S63 whether or not interruption retesting of the sample of the preceding rack 101 has been completed. This determination is repeated (i.e., the withdrawn state is maintained) until the sample (the sample container 100), which is the subject of retesting, is returned from the measurement unit 3 to the preceding rack 101 as shown in STATE 32 of FIG. 25. When the sample (the sample container 100), which is the subject of retesting, is returned from the measurement unit 3 to the preceding rack 101, the processing proceeds to step S64, at which the subsequent rack 101 returns to the previous position, following the movement of the preceding rack 101.

When it is determined at step S61 that a sample for which retesting has been determined to be necessary is not present in the preceding rack 101 (and when a sample for which retesting has been determined to be necessary is present in the subsequent rack 101), the processing proceeds to step S65, at which the CPU 51a controls the sample transporting apparatus 4 such that the sample (the sample container 100) for which retesting is necessary is transported again in the upstream transporting direction (the arrow X2 direction) to the loading position 43a. Then, in the container loading process shown in step S1 of FIG. 10, the sample to be retested is loaded into the measurement unit 3 and interruption retesting is performed, accordingly. In the above manner, interruption retesting for the subsequent rack 101 is performed at step S49. Note that since retesting of the samples of the subsequent rack 101 is performed after necessity/unnecessity determination for retesting has been completed for all the samples of the preceding rack 101, the process at step S65 is performed after the preceding rack 101 has been collected.

When interruption retesting at step S49 ends, the processing returns to step S44, at which it is determined whether or not a sample for which retesting is necessary is present in the preceding rack 101 or in the subsequent rack 101. Note that when a necessity/unnecessity determination result obtained during the interruption retesting indicates presence of a sample for which retesting has been determined to be necessary, the processing proceeds to step S49, at which interruption retesting is performed on the sample for which retesting has newly been determined to be necessary. Further, in practice, the above steps S43 to S45 and S49 are performed in parallel.

At step S46, the subsequent rack 101 is transversely fed to the rack collection position 43d after the tenth (the last) sample container 100 of the subsequent rack 101 has been returned to the subsequent rack 101. At step S47, it is determined, while the subsequent rack 101 is disposed at the rack collection position 43d, whether or not the samples in the subsequent rack 101 include a sample for which retesting has been determined to be necessary. To be specific, when the subsequent rack 101 is disposed at the rack collection position 43d, necessity/unnecessity determination for retesting has already been completed for the first to eighth sample containers and necessity/unnecessity determination for retesting is waited to be performed on the ninth and tenth samples. Then, if it is determined that retesting is necessary for the ninth or tenth sample, interruption retesting thereof is performed at step S48. The interruption retesting at step S48 is the same process as the interruption retesting at the above step S49.

On the other hand, when no sample in the subsequent rack 101 requires retesting, it is determined at step S50 whether or not necessity/unnecessity determination for retesting has been completed for all the samples of the subsequent rack 101. When necessity/unnecessity determination has been completed for all the samples, the rack feed-out part 46 collects the subsequent rack 101 located at the rack collection position 43d into the analyzed rack holder 42 and the transporting process of the subsequent rack 101 ends at step S51, accordingly. Whereas, when necessity/unnecessity determination for retesting has not been completed for all the samples of the subsequent rack 101, the standby state of the subsequent rack 101 at the rack collection position 43d is maintained at step S52. Note that the processes at steps S46 to S48 and steps S50 to S52, which are performed for the subsequent rack 101, are the same as the processes at steps S25 to S27 and steps S29 to S31 shown in FIG. 12, respectively, which are performed for the preceding rack 101.

Note that, the present embodiment gives a description of the transporting process of the subsequent rack 101 (the rack 101 holding the eleventh to twentieth samples), in which the subsequent rack is, for the sake of convenience in the description, referred to as a "subsequent rack" even after the preceding rack 101 holding the first to tenth samples has been collected. However, in practice, the subsequent rack 101 (the rack 101 holding the eleventh to twentieth samples) is, after the preceding rack 101 holding the first to tenth samples has been collected, treated as a "preceding rack".

As described above in the present embodiment, when the control apparatus 5 (the CPU 51a) determines retesting to be necessary for a sample of a particular sample container 100 held in a rack 101, the transporting direction of the first belt 431 (see FIG. 6) or the second belt 432 (see FIG. 6), which transports the rack 101, is changed from the downstream transporting direction (the arrow X1 direction) to the upstream transporting direction (the arrow X2 direction), and the sample transporting apparatus 4 is controlled so as to transport again the sample container 100, which is the subject of retesting, in the upstream transporting direction (the arrow X2 direction) to the loading position 43a (see FIG. 2). In this manner, when sample retesting is necessary, a sample container 100 that is a subject of retesting can be transported in the upstream transporting direction (the arrow X2 direction) directly to the loading position 43a without returning the rack 101 to the rack feed-in position 43b (see FIG. 2). Accordingly, as compared to a case where the rack 101 is transported passing through the loading position 43a to the rack feed-in position 43b and then transported again in the downstream transporting direction (the arrow X1 direction) to the loading position 43a, the moving distance of the rack 101 in the case of performing retesting can be reduced by a round trip distance between the loading position 43a and the rack feed-in position 43b. As a result, a time required for transporting the rack 101 for sample retesting can be reduced. Accordingly, sample retesting can be performed efficiently.

Further, in the present embodiment, after the measurement unit 3 has obtained, for retesting, a sample from a sample container 100 that is a subject of retesting, the control apparatus 5 (the CPU 51a) changes the transporting direction of the first belt 431 (see FIG. 6) or the second belt 432 (see FIG. 6), which transports the rack 101, from the upstream transporting direction (the arrow X2 direction) to the downstream transporting direction (the arrow X1 direction), and controls the sample transporting apparatus 4 so as to transport, to the loading position 43a, a sample container 100 from which a sample has not been loaded into the measurement unit 3. In this manner, after the rack 101 is transported in the upstream transporting direction (the arrow X2 direction) and a sample contained in a sample container 100, which is a subject of retesting, is retested, a sample container 100 from which a sample is to be loaded next can be transported to the loading position 43a promptly.

Still further, in the present embodiment, the control apparatus 5 (the CPU 51a) is configured to control the rack feed-in part 411 so as to feed the subsequent rack 101 to the rack feed-in position 43b (see FIG. 2) when retesting has been determined to be unnecessary for all the samples held in container accommodating portions 101b that are, from among the ten container accommodating portions 101b of the preceding rack 101, located farther in the downstream transporting direction (the arrow X1 direction) than the seventh container accommodating portion 101b. In this manner, even before the entire testing process of the preceding rack 101, which includes retesting, is completed, the following subsequent rack 101 can be fed to the rack feed-in position 43b at the time when retesting has been determined to be unnecessary for all the samples held in the container accommodating portions 101b of the preceding rack 101, the container accommodating portions 101b being farther, in the downstream transporting direction (the arrow X1 direction), than the seventh container accommodating portion 101b. Accordingly, processing on the following subsequent rack 101 can be started promptly.

Still further, in the present embodiment, the control apparatus 5 (the CPU 51a) is configured to determine, when retesting of a sample has been performed, that further retesting of the sample is unnecessary. Accordingly, once a sample is retested, the sample is not retested again. This prevents stagnation in the testing process in the case where retesting is repeatedly performed. This allows the system to efficiently perform the testing process. Also, necessity/unnecessity determination for retesting of a sample is performed at the time when retesting of the sample has been performed. Accordingly, when retesting of the sixth sample has been performed, further retesting of the sixth sample is determined to be unnecessary before measurement results of the retesting of the sixth sample are obtained (i.e., before the predetermined time (75 seconds) has elapsed after the loading of the sixth sample into the measurement unit 3). This allows the subsequent rack 101 to be fed to the rack feed-in position 43b more promptly.

Still further, there provided in the present embodiment are: the unanalyzed rack holder 41 for storing a plurality of racks 101; and the rack feed-in part 411 for moving, only in the arrow Y2 direction (see FIG. 2), a rack 101 stored in the unanalyzed rack holder 41 from the unanalyzed rack holder 41 to the rack feed-in position 43b. In the present embodiment, even in the case where retesting is, after the subsequent rack 101 has been fed to the rack feed-in position 43b, performed on a sample (the seventh or subsequent sample) of the preceding rack 101, the preceding rack 101, which is reversely fed in the upstream transporting direction (the arrow X2 direction) to the loading position 43a, does not interfere with the subsequent rack 101 having been fed to the rack feed-in position 43b. Accordingly, there is no need to provide a mechanism for withdrawing the subsequent rack 101 from the rack feed-in position 43b into the unanalyzed rack holder 41. As a result, it is only necessary for the rack feed-in part 411 to be configured to move only in the arrow Y2 direction (see FIG. 2). Accordingly, in relation to the feature of directly returning the preceding rack 101 to the loading position 43a for sample retesting, it is not necessary for the rack feed-in part 411 to have a function to withdraw the subsequent rack 101 from the rack feed-in position 43b. This prevents the system from being complex, and yet realizes prompt execution of the testing process.

Still further, in the present embodiment, the control apparatus 5 (the CPU 51a) is configured to control the sample transporting apparatus 4 so as to transport, when the samples of all the sample containers 100 held in a rack 101 have undergone loading into the measurement unit 3, the rack 101 to the rack collection position 43d (the collectable position; see FIG. 2), and to control the rack feed-out part 46 so as to transfer, when retesting has been determined to be unnecessary for the samples of all the sample containers 100 held in the rack 101, the rack 101 located at the rack collection position 43d to the analyzed rack holder 42. Accordingly, when there is a possibility of retesting of a sample of the preceding rack 101, the preceding rack 101 is kept disposed at the rack collection position 43d (the collectable position). Thus, the preceding rack 101 can be promptly transported in the upstream transporting direction (the arrow X2 direction) to the loading position 43a if retesting is necessary for a sample of the preceding rack 101. This allows retesting to be performed promptly. Whereas, if no sample in the preceding rack 101 requires retesting, the preceding rack 101 can be collected from the rack collection position 43d (the collectable position) promptly.

Still further, in the present embodiment, the control apparatus 5 (the CPU 51a) is configured to determine, for a sample container 100 having been transported to the loading position 43a, whether or not a piece of sample identification information (sample ID) obtained by the bar code reader 44 coincides with a piece of sample identification information (sample ID) obtained by the bar code reader 356 of the measurement unit 3. The control apparatus is also configured to perform, when these pieces of identification information (sample IDs) do not coincide with each other, error handling so as to cause the display 52 to display a message indicating the noncoincidence. Accordingly, based on sample identification information (sample ID) obtained by the bar code reader 44 during the process of transporting a rack 101 to the loading position 43a, and sample identification information (sample ID) obtained by the bar code reader 356 when a sample container 100 is loaded into the measurement unit 3 for testing (or retesting) of the sample therein, it can be confirmed whether or not the sample container 100 loaded within the measurement unit 3 is a sample container 100 (a sample) to be tested (or retested). Therefore, even if a sample container 100 that is not a subject of testing (or retesting) is erroneously disposed at the loading position 43a, the sample container 100 can be determined not to be a subject of testing (or retesting) prior to the measurement unit 3 performing the measurement process, and a user can be notified of the determination.

Still further, in the present embodiment, the control apparatus 5 (the CPU 51a) is configured to act as determination means for determining whether or not retesting is necessary. Therefore, as opposed to a case where the control apparatus 5 (the CPU 51a) and the determination means are separately provided, the control apparatus 5 (the CPU 51a) is able to: obtain measurement results for a sample from the measurement unit 3; determine whether or not retesting of the sample is necessary; and control the operations of the sample transporting apparatus 4 based on the necessity/unnecessity determination. Accordingly, the configuration of the blood analyzer 1 can be simplified.

Note that the embodiment disclosed herein is merely illustrative in all aspects and should not be recognized as being restrictive. The scope of the present invention is defined by the scope of the claims rather than by the description of the above embodiment, and includes meaning equivalent to the scope of the claims and all modifications within the scope.

For instance, the present embodiment describes the blood analyzer as an example of the sample testing system. However, the present invention is not limited thereto. The present invention may be applied to a sample testing system that is not a blood analyzer as long as the sample testing system includes a transporting apparatus for transporting a sample rack that is capable of holding a plurality of samples.

Figure 26:
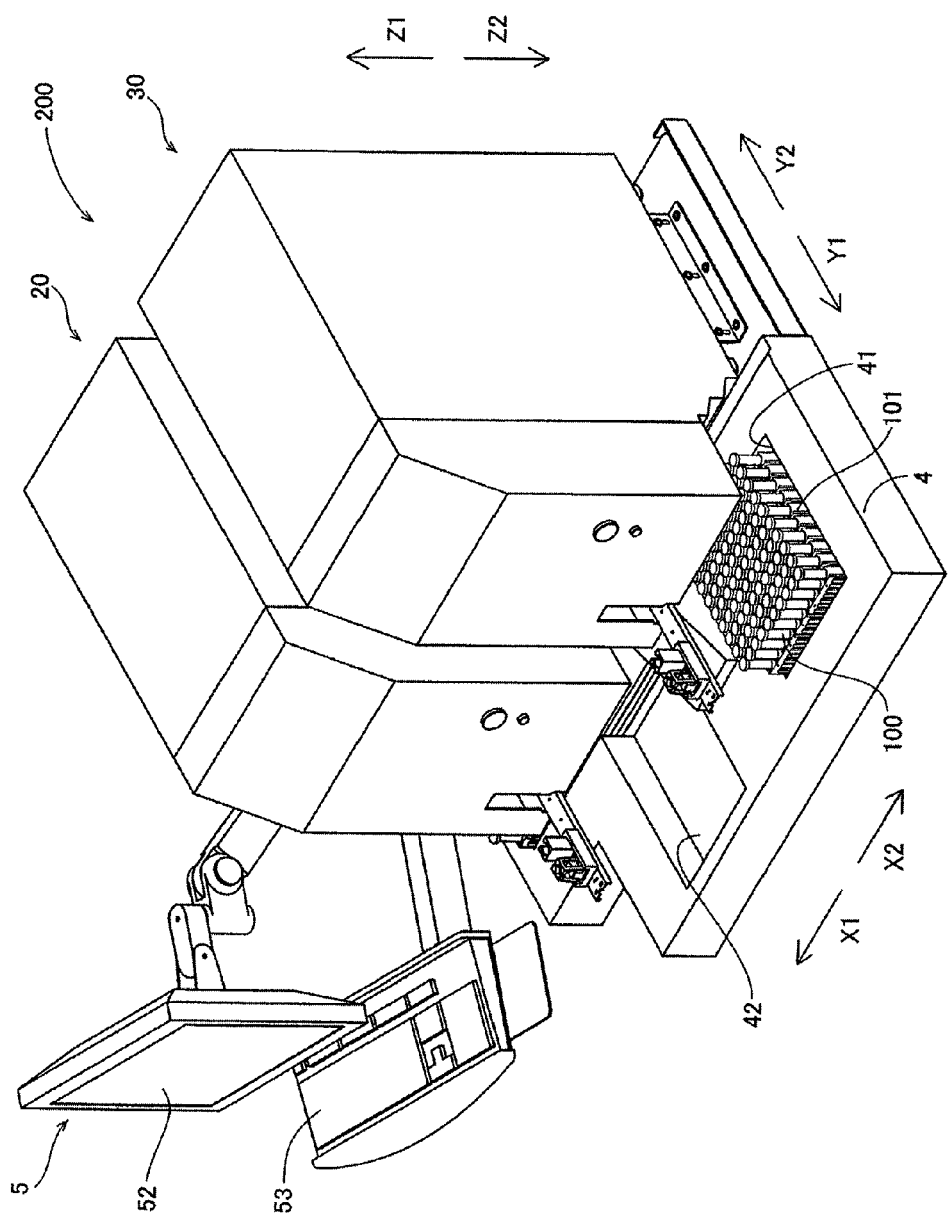
FIG. 26 is a perspective view showing a variation of the blood analyzer according to the embodiment shown in FIG. 1.

Further, the present embodiment describes the blood analyzer that includes one measurement unit, as an example of the sample testing system. However, the present invention is not limited thereto. For example, as shown in FIG. 26, the blood analyzer may be a blood analyzer 200 that includes two measurement units 20 and 30, or may be a blood analyzer that includes three or more measurement units.

Still further, the present embodiment describes a configuration in which the control apparatus determines whether or not retesting is necessary. However, the present invention is not limited thereto. The host computer, which is connected to the control apparatus so as to be able to transmit/receive data to/from the control apparatus, may determine whether or not retesting is necessary. To be specific, the configuration may be such that: the control apparatus transmits, via the communication interface to the host computer, measurement data received from the measurement unit; the host computer determines based on the measurement data whether or not retesting is necessary; and the control apparatus receives, from the host computer via the communication interface, a result of the determination as to whether or not retesting is necessary.

Still further, as an example of computer programs, the present embodiment describes two computer programs that are the measurement process program and the sampler operation process program. However, the present invention is not limited thereto. The computer program of the present invention may be a single computer program that includes the contents of the measurement process program and the sampler operation process program.

Still further, as an example of a control apparatus, the present embodiment describes the CPU of the control apparatus that executes the measurement process program and the sampler operation process program so as to control both the measurement unit and the sample transporting apparatus (sampler). However, the present invention is not limited thereto. In the present invention, a control apparatus dedicated for the sample transporting apparatus may be provided separately from a control apparatus for controlling the measurement unit. In this case, the control apparatus dedicated for the sample transporting apparatus may be provided not as a separate control apparatus but as a part of the sample transporting apparatus.

Figure 17:
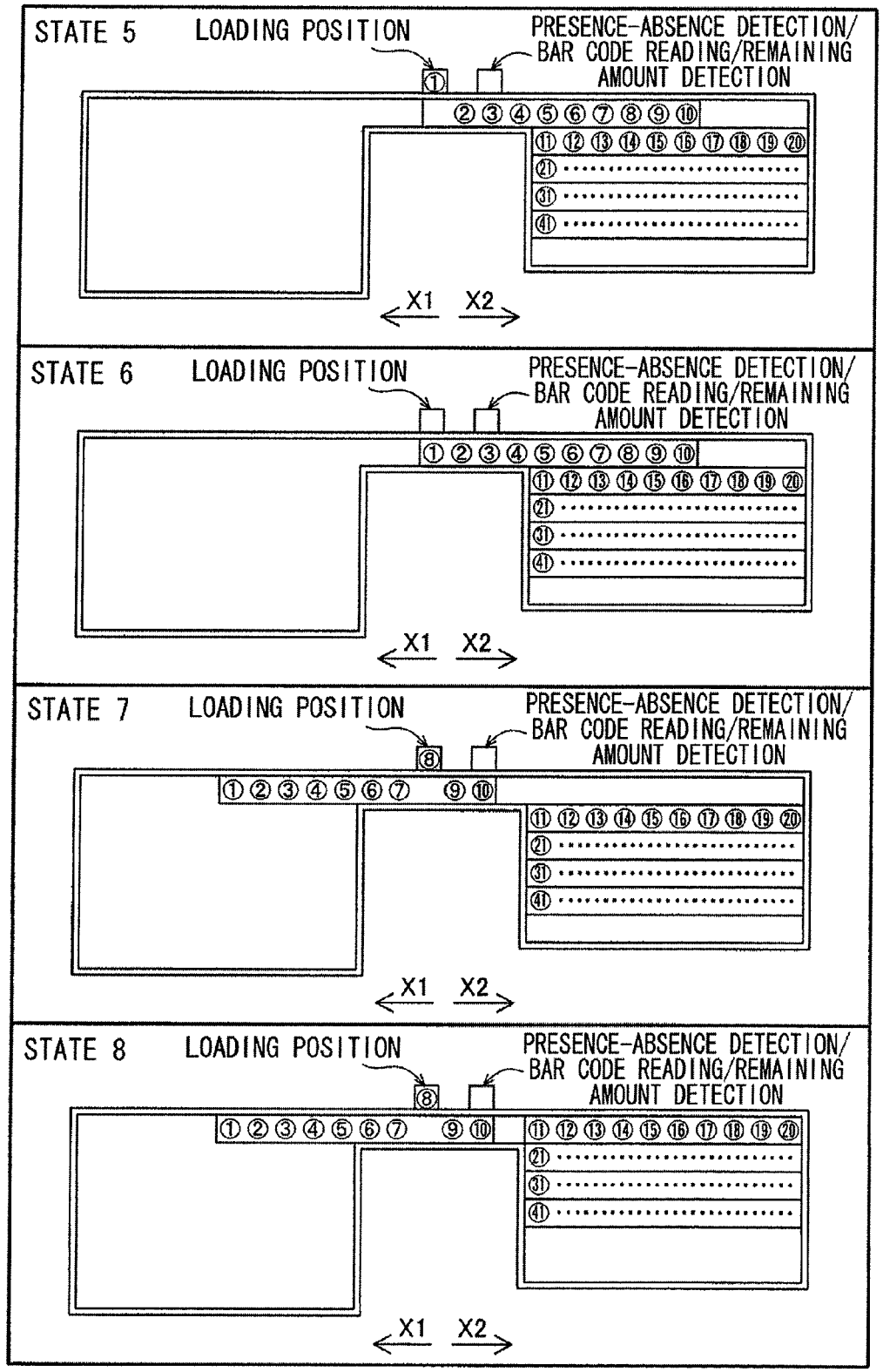
FIG. 17 shows positional relationships among the racks, the sample containers, and the positions in the blood analyzer according to the embodiment shown in FIG. 1.
Figure 18:
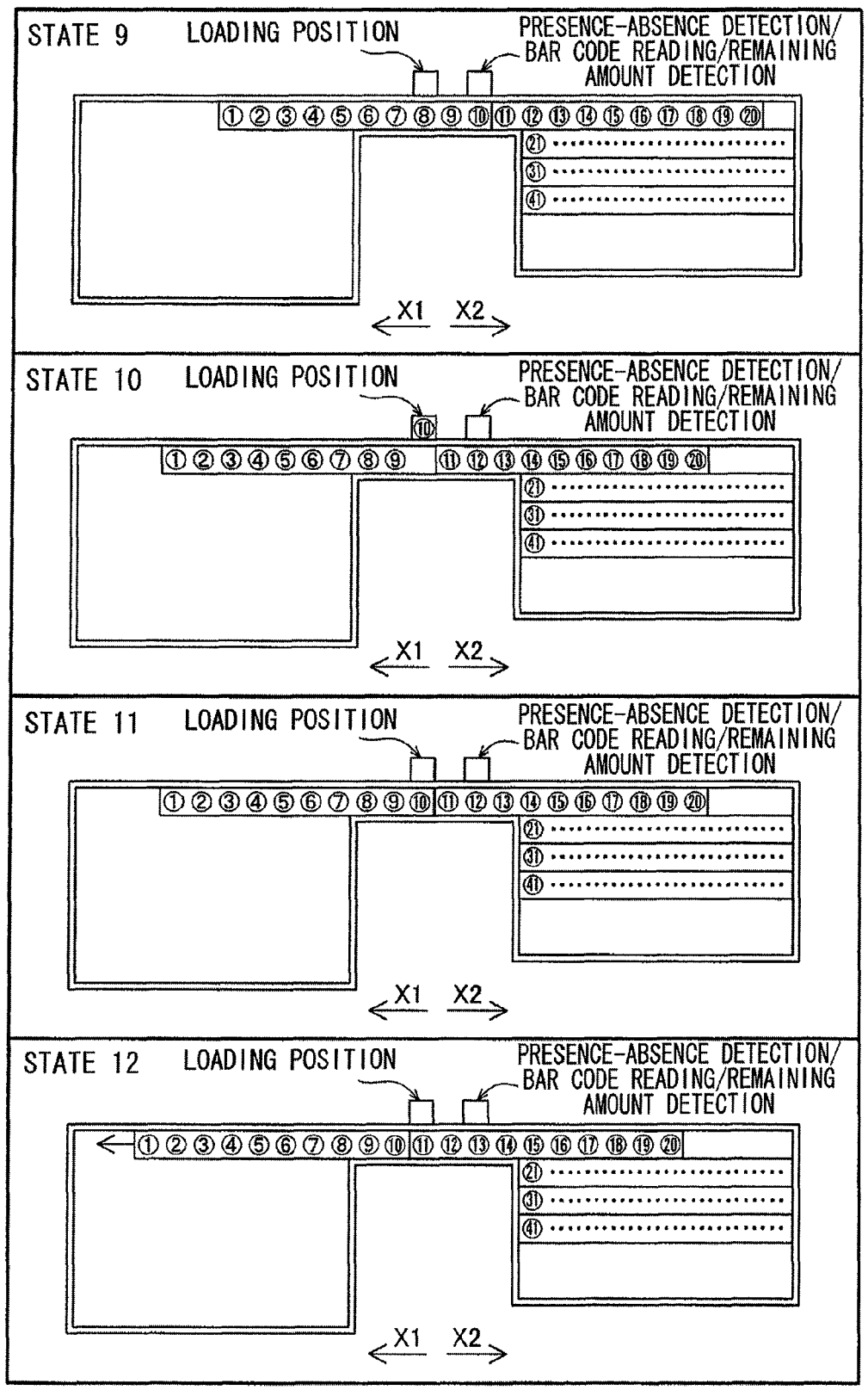
FIG. 18 shows positional relationships among the racks, the sample containers, and the positions in the blood analyzer according to the embodiment shown in FIG. 1.

Still further, the present embodiment describes a configuration example in which when retesting is determined to be unnecessary for the first to sixth samples of the preceding rack (all the samples held in the container accommodating portions 101b located farther, in the downstream transporting direction (the arrow X1 direction), than the seventh sample), the subsequent rack is immediately fed to the rack feed-in position as shown in STATE 8 of FIG. 17. However, the present invention is not limited thereto. In the present invention, although the subsequent rack can be fed when retesting has been determined to be unnecessary for the sixth sample of the preceding rack, the subsequent rack does not have to be fed immediately. For example, the subsequent rack may be fed to the rack feed-in position after it is determined whether or not retesting is necessary for the seventh sample of the preceding rack.

Still further, the present embodiment describes a configuration example in which retesting is determined to be unnecessary for a sample on which retesting has already been performed once. However, the present invention is not limited thereto. The control apparatus may be configured to perform necessity/unnecessity determination for retesting again for a sample on which retesting has been performed once. In this case, retesting may be determined to be unnecessary for a sample on which retesting has been performed twice, or necessity/unnecessity determination for retesting may be repeatedly performed until retesting is determined to be unnecessary.

Still further, the present embodiment describes a configuration example in which the rack feed-in part is controlled so as to feed the subsequent rack based on the necessity/unnecessity determination for sample retesting. However, the present invention is not limited thereto. In the present invention, the control apparatus may be configured to control the rack feed-in part so as to feed the subsequent rack based on the state of the sample transporting apparatus or the measurement unit. For example, assume a case where synchronization failure has occurred in the sample transporting apparatus with respect to synchronization between the sample transporting apparatus and the control apparatus and thereby monitoring of the positions of the racks becomes impossible, or a case where the measurement unit has failed in loading a sample container. In these cases, it is necessary to return the preceding rack toward the upstream side of the transporting direction (the arrow X2 direction), such that the preceding rack is fed beyond the feed-in limit position and then disposed at the rack feed-in position. Accordingly, the rack feed-in part may be controlled so as to feed the subsequent rack when the state as described above is resolved in the sample transporting apparatus or in the measurement unit.

Still further, the present embodiment describes a configuration example in which when a rack is disposed at the feed-in limit position (i.e., the position that is nearest to, but does not overlap with, the rack feed-in position), the position at which the loading into the measurement unit is performed is located at the position of the seventh sample container of the rack. However, the present invention is not limited thereto. In the present invention, the loading position may be located at the position of the sixth or previous sample container or the position of the eighth or subsequent sample container of the rack. In this case, the number of samples in the preceding rack, for which retesting has been determined to be unnecessary, the number being used as a reference for determination at step S41 of FIG. 13 as to whether or not to feed the subsequent rack to the rack feed-in position, varies in accordance with the location of the loading position.

Still further, the present embodiment describes an example of the manner of obtaining a sample by the measurement unit, in which: the measurement unit removes, from a sample rack, a sample container disposed at the sample loading position; the sample container is loaded into the measurement unit; and a sample contained in the sample container is aspirated in the measurement unit. However, the present invention is not limited thereto. For example, the scope of the present invention includes a different manner, in which the measurement unit aspirates the sample contained in the sample container disposed at the sample loading position, while the sample container is kept being held in the sample rack.

What is claimed is:

1. A sample testing system comprising:
   a transporting apparatus comprising: a first rack holder that holds a sample rack comprising a plurality of holding positions, each holding position holding a sample container, and that provides the sample rack to a first position on a rack transporting path that extends between the first position and a second position; a second rack holder that holds the sample rack after testing; a rack feeder that feeds a tested sample rack from the second position on the rack transporting path to the second rack holder; and first and second transporting members each configured to transport sample racks along the rack transporting path between the first position to the second position through a third position on the rack transporting path that is between the first and second positions, wherein the first and second transporting members are each configured to transport the sample racks in a first direction and in a second direction that is opposite to the first direction;
   a testing apparatus configured to perform an initial test and a retest on a sample contained in one or more of the sample containers held in the plurality of holding positions, each of the initial test and the retest comprising obtaining a sample from a sample container located at the third position and performing a measurement on the obtained sample; and
   a controller including a memory under control of a processor, the memory storing instructions enabling the processor to carry out operations comprising:
      controlling the first transporting member so as to transport a first sample rack in the first direction from the first position to the second position along the rack transporting path such that each sample container held in the first sample rack is sequentially brought to the third position for subjecting the samples to the initial test;
      determining for each sample subjected to the initial test whether the sample is required to be subjected to the retest on the basis of the result of the initial test while the first sample rack is on the rack transporting path;
      controlling the second transporting member so as to transport a second sample rack in the first direction such that the second sample rack follows the first sample rack while the first sample rack is on the rack transporting path;
      controlling, when retest of any sample in a sample container held on the first sample rack is required:
         the second transporting member so as to reversely transport the second sample rack in the second direction along the rack transporting path to make a space for allowing the first sample rack to be brought to the third position; and
         the first transporting member so as to reversely transport the first sample rack in the second direction along the rack transporting path and to stop the reverse transportation when the sample container corresponding to the sample to be retested is located at the third position; and
      controlling, in response to a determination that all samples of the sample containers held on the first sample rack are not required to be subjected to a retest, the rack feeder to feed the first sample rack to the second rack holder.

2. The sample testing system according to claim 1, wherein
   the memory further stores information about a distance from the first position to the third position,
   the transporting apparatus comprises a moving distance obtaining part for obtaining information about a distance that the first sample rack or the second sample rack transported in the first direction has moved from the first position, and
   controlling the first transporting member and controlling the second transporting member are based on:
      the stored information about the distance from the first position to the third position;
      the information obtained by the moving distance obtaining part; and
      information about one of the sample holding positions that holds a sample container containing a sample to be retested.

3. The sample testing system according to claim 1, wherein
   the first rack holder further comprises a rack feeder for feeding the sample rack to the first position,
   the first and second transporting members are configured to receive, at the first position, the first sample rack that is fed by the rack feeder of the first rack holder and the second sample rack that is fed by the rack feeder of the first rack holder following the first sample rack, and to transport the first and second sample racks in the first direction towards the third position, and
   the operations further comprise
      controlling, in response to a determination that all samples of the sample containers held on the first sample rack are not required to be subjected to a retest, the feeding, by the rack feeder of the first rack holder, of the second sample rack to the first position.

4. The sample testing system according to claim 3, wherein
   the controlling the feeding by the rack feeder of the first rack holder is carried out by controlling the rack feeder of the first rack holder so as to feed the second sample rack to the first position when a predetermined holding position of the first sample rack is located at the third position and the controller determines that retesting is unnecessary for all samples of the first sample rack accommodated in sample containers held at holding positions located between the second position and the third position.

5. The sample testing system according to claim 1, further comprising a first identification information obtaining part, located at a fourth position on the transporting path between the first position and the third position, for obtaining identification information from each sample container held in the first and second sample racks transported by the transporting apparatus, wherein
   the testing apparatus comprises a second identification information obtaining part for obtaining identification information from each sample container that has been transported to the third position.

6. The sample testing system according to claim 5, wherein the operations further comprise:
- determining whether or not the identification information, that has been obtained by the first identification information obtaining part, coincides with the identification information that has been obtained by the second identification information obtaining part; and
- notifying, when these identification information do not coincide with each other.

7. The sample testing system according to claim 1, wherein the controller determines whether or not retesting of a sample is necessary based on a measurement result of the sample, wherein the determining comprises:
- obtaining, from the testing apparatus, a measurement result of a sample;
- transmitting the measurement result to the host computer; and
- obtaining, from the host computer, a determination result which indicates whether or not retesting of the sample is necessary.

8. The sample testing system according to claim 1, wherein after the initial tests are completed for each sample of the first sample rack, the controller controls the first transporting member so as to transport the first sample rack in the first direction along the rack transporting path to the second position.

* * * * *